US012613204B2

(12) United States Patent
Im et al.

(10) Patent No.: US 12,613,204 B2
(45) Date of Patent: Apr. 28, 2026

(54) METHOD FOR ANALYZING ENDOSOMAL ESCAPE EFFICIENCY OF DRUG DELIVERY PARTICLES

(71) Applicant: SEOUL NATIONAL UNIVERSITY R&DB FOUNDATION, Seoul (KR)

(72) Inventors: Hyung Jun Im, Gyeonggi-do (KR); Jeong Bin Park, Gyeonggi-do (KR); So Min Lee, Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 196 days.

(21) Appl. No.: 18/722,940

(22) PCT Filed: Dec. 22, 2022

(86) PCT No.: PCT/KR2022/021076
§ 371 (c)(1),
(2) Date: Jun. 21, 2024

(87) PCT Pub. No.: WO2023/121347
PCT Pub. Date: Jun. 29, 2023

(65) Prior Publication Data
US 2025/0060325 A1 Feb. 20, 2025

(30) Foreign Application Priority Data

Dec. 22, 2021 (KR) ........................ 10-2021-0185172
Dec. 22, 2022 (KR) ........................ 10-2022-0181667

(51) Int. Cl.
*G01N 24/08* (2006.01)
*G01N 33/15* (2006.01)

(52) U.S. Cl.
CPC ........... *G01N 24/088* (2013.01); *G01N 33/15* (2013.01)

(58) Field of Classification Search
CPC ...... G01N 24/088; G01N 33/15; G01N 15/00; G01N 15/10; G01N 24/08; G01N 24/10; G01N 33/48; G01R 33/28; G01R 33/44; G01R 33/56; G01R 33/60; B82Y 15/00; B82Y 25/00
See application file for complete search history.

(56) References Cited

U.S. PATENT DOCUMENTS

2023/0242554 A1* 8/2023 Okamoto ............. A61K 31/555
514/185

FOREIGN PATENT DOCUMENTS

JP        2006-028030 A     2/2006
KR    10-2011-0068323 A     6/2011
(Continued)

OTHER PUBLICATIONS

International Search Report for PCT/KR2022/021076 mailed on Mach 30, 2023.
(Continued)

*Primary Examiner* — G.M. A Hyder
(74) *Attorney, Agent, or Firm* — The PL Law Group, PLLC

(57) ABSTRACT

A method for quantitatively analyzing endosomal escape efficiency of drug delivery particles includes measuring magnetic resonance signals (MR signals) reflected upon emission of electromagnetic waves (for example, radio waves) into cells having iron oxide-carrying particles ingested thereinto, with the aid of a magnetic resonance imaging device, and obtaining a change rate of magnetic relaxation with time from the measurements.

6 Claims, 32 Drawing Sheets

(56)                    References Cited

FOREIGN PATENT DOCUMENTS

Figure 2A:
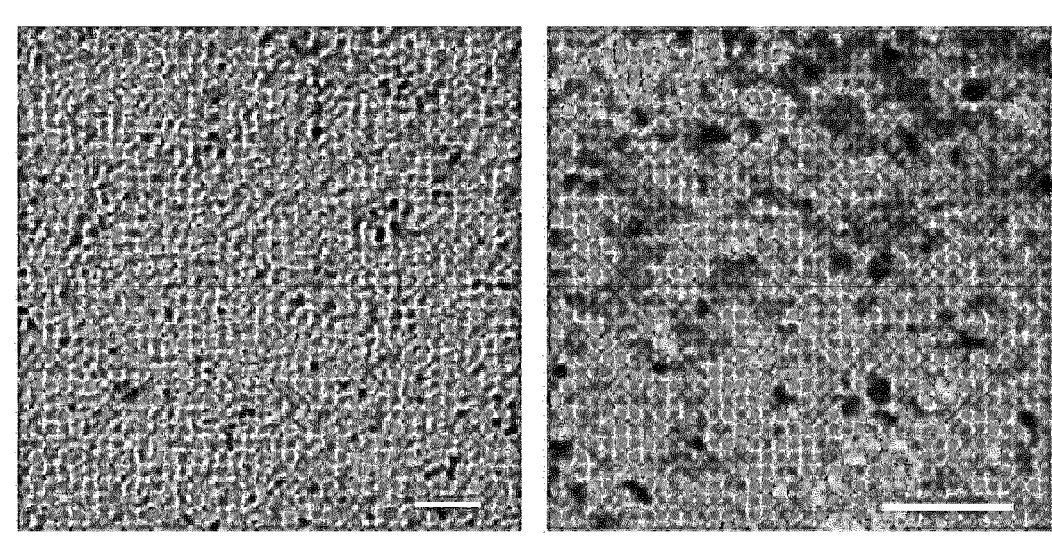

| | | | |
|---|---|---|---|
| KR | 10-2013-0113575 | A | 10/2013 |
| KR | 10-2017-0133930 | A | 12/2017 |
| KR | 10-2019-0096148 | A | 8/2019 |

OTHER PUBLICATIONS

Michael J. Munson et al., "A high-throughput Galectin-9 imaging assay for quantifying nanoparticle uptake, endosomal escape and functional RNA delivery", Communications Biology, 2021, 4:211, https://doi.org/10.1038/s42003-021-01728-8.

Thomas Martens, "Optimizing delivery of gene nanomedicines towards the retina via intravitreal administration", Universiteit GENT, Laboratory for Gemeral Biochemistry and Physical pharmacy, 2014.

Jinying Liang et al., "Lipid-coated iron oxide nanoparticles for dual-modal imaging of hepatocellular carcinoma", International Journal of Nanomedicine, 2017, vol. 12, pp. 2033-2044.

Michel Modo et al., "Cellular MR imaging", Molecular Imaging., vol. 4, No. 3, Jul. 2005, pp. 143-164.

WJ Rogers et al., "Technology insight: in vivocell tracking by use of MRI", Nature Clinical Practice, Oct. 2006, vol. 3, No. 10, pp. 554-562.

D Kim et al., "The present status of cell tracking methods in animal models using magnetic resonance imaging technology", Mol Cells, 2007, vol. 23, No. 2, pp. 132-137.

* cited by examiner

FIG. 1A

FIG. 1B

R2 MR phatom

FIG. 3A $y = 130.0x + 8.725$
$R^2 = 0.8687$

Time elapsed after treament
(h)

Trends of $R_1$ according to Incubation Time

FIG. 14B

FIG. 14C

METHOD FOR ANALYZING ENDOSOMAL ESCAPE EFFICIENCY OF DRUG DELIVERY PARTICLES

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2022/021076, filed Dec. 22, 2022, which claims priority to the benefit of Korean Patent Application Nos. 10-2021-0185172 filed on Dec. 22, 2021 and 10-2022-0181667 filed on Dec. 22, 2022 in the Korean Intellectual Property Office, the entire contents of which are incorporated herein by reference.

BACKGROUND

1. Technical Field

The present invention relates to a method for analyzing endosomal escape efficiency of drug delivery particles.

2. Background Art

Drug delivery particles such as lipid nanoparticles (LNPs), liposomes, and the like are introduced into cells through the formation of organelles called endosomes when flowing into the cells. For effective delivery of substances in the drug delivery particles and expression of the delivered substances, particles which are introduced into the cells and surrounded by the endosomes should be able to escape the endosomes and move to a nucleus or perform functions thereof in the cytoplasm. Since this endosomal escape efficiency varies depending on the particles, a number of researches on particles capable of loading target substances are being carried out in the field of new drug development today. However, there is no method to quantitatively analyze endosomal escape efficiency of the drug delivery particles.

Magnetic resonance imaging (MRI) is an imaging method that obtains arbitrary tomographic images of the living body using magnetic fields generated by a magnetic force. In MRI, various images can be obtained by controlling imaging variables. Typically, an imaging method that makes tissues with a short T1 relaxation time appear bright is referred to T1-weighted imaging, while an imaging method that makes tissues with a short T2 relaxation time appear dark is referred to T2-weighted imaging. In addition, by controlling imaging parameters to have an appropriate T1 or T2 relaxation time, it is possible to obtain T1 or T2-weighted image most suitable for molecular and cellular images.

Imaging contrast agents used in magnetic resonance imaging are generally divided into T1 contrast agent and T2 contrast agent, and these imaging contrast agents have an effect of reducing the relaxation time when measuring T1 and T2, respectively (M Modo, M Hoehn, J W Bulte, Cellular M R imaging, Mol Imaging, 4, 143 (2005); W J Rogers, H Meyer, C M Kramer, Technology insight: in vivocell tracking by use of MRI, Nat ClinPrac, 3, 554 (2006); D Kim, K S Hong, J Song, The present status of cell tracking methods in animal models using magnetic resonance imaging technology, Mol Cells, 23, 132 (2007)). In particular, iron oxide-based T2 contrast agent has a very significant effect of reducing the T2 relaxation time, and exhibits a strong imaging contrast effect due to a decrease in the T2 relaxation time.

SUMMARY

An object of the present invention is to provide a method for quantitatively analyzing endosomal escape efficiency of drug delivery particles.

1. A method for analyzing endosomal escape efficiency of drug delivery particles, including: measuring, in a cell into which particles having iron oxides loaded therein are ingested, a magnetic resonance signal which changes as the iron oxides are released from the particles to the cell: obtaining a graph representing changes in a magnetic relaxation rate due to a lapse of time from the magnetic resonance signal: obtaining a change rate of the magnetic relaxation rate in an arbitrary time interval of the graph; and obtaining an endosomal escape rate of the particles by substituting the change rate of the magnetic relaxation rate into Equation 1 below:

$$\text{Endosomal escape rate (\%)} = (\text{Change rate of magnetic relaxation rate in cell having particles ingested thereinto} \div (\text{Magnetic relaxation rate of total iron oxides loaded in particles before endosomal escape} - \text{Magnetic relaxation rate of total free iron oxides released from particles due to the endosomal escape})) \times 100. \quad \text{[Equation 1]}$$

2. The method for analyzing endosomal escape efficiency of drug delivery particles according to the above 1, wherein the magnetic relaxation rate is an $R_2$ magnetic relaxation rate.

3. The method for analyzing endosomal escape efficiency of drug delivery particles according to the above 1, further comprising: obtaining a total concentration of intracellular ingested iron oxides; and obtaining a difference between a total $R_2$ magnetic relaxation rate of the iron oxides loaded in the particles before the endosomal escape and a total $R_2$ magnetic relaxation rate of the iron oxides released from the particles to the cell due to the endosomal escape, by substituting the total concentration of the intracellular ingested iron oxides into Equation 2 below:

$$\{(\text{Total magnetic relaxation rate of iron oxides loaded in particles}) - (\text{Total magnetic relaxation rate of free iron oxides released from particles to cell})\} = \text{Intracellular iron oxide concentration} \times (\text{Magnetic relaxation rate per unit concentration of iron oxides loaded in particles} - \text{Magnetic relaxation rate per unit concentration of free iron oxides}). \quad \text{[Equation 2]}$$

4. The method for analyzing endosomal escape efficiency of drug delivery particles according to the above 1, wherein the particles are any one selected from the group consisting of lipid nanoparticles, liposomes, micelles, polymer nanoparticles, dendrimer nanoparticles, DNA nanostructures, metal nanoparticles, carbon nanotubes, fullerenes and virus-like particles.

5. The method for analyzing endosomal escape efficiency of drug delivery particles according to the above 1, wherein the particles have a size of 50 to 250 nm.

6. The method for analyzing endosomal escape efficiency of drug delivery particles according to the above 1, wherein the iron oxides have a size of 1 to 20 nm.

The present invention provides a method for analyzing endosomal escape efficiency of drug delivery particles.

The method for analyzing endosomal escape efficiency of drug delivery particles of the present invention may quantitatively analyze the endosomal escape efficiency of drug delivery particles by using magnetic resonance imaging signals which vary depending on an amount of iron oxides released from the drug delivery particles ingested into cells.

US 12,613,204 B2

3
BRIEF DESCRIPTION OF THE DRAWINGS

Figure 1A:
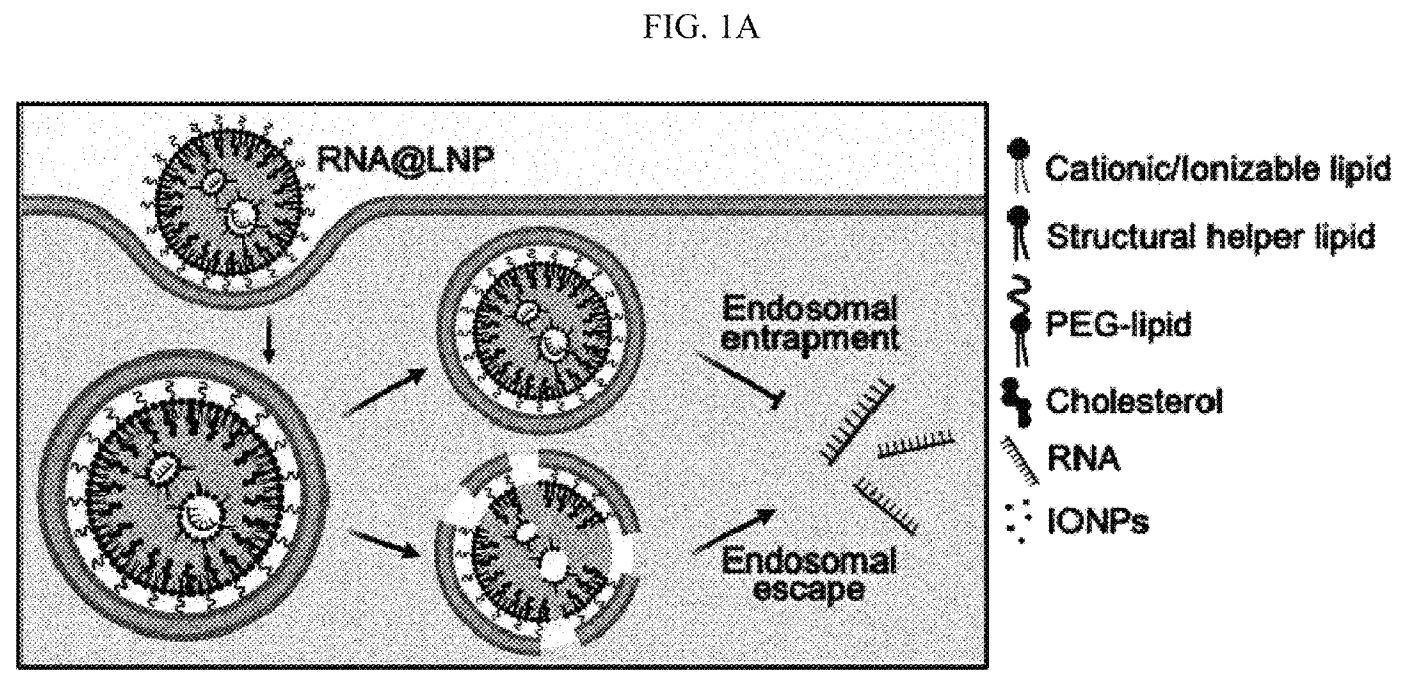
Figure 1B:
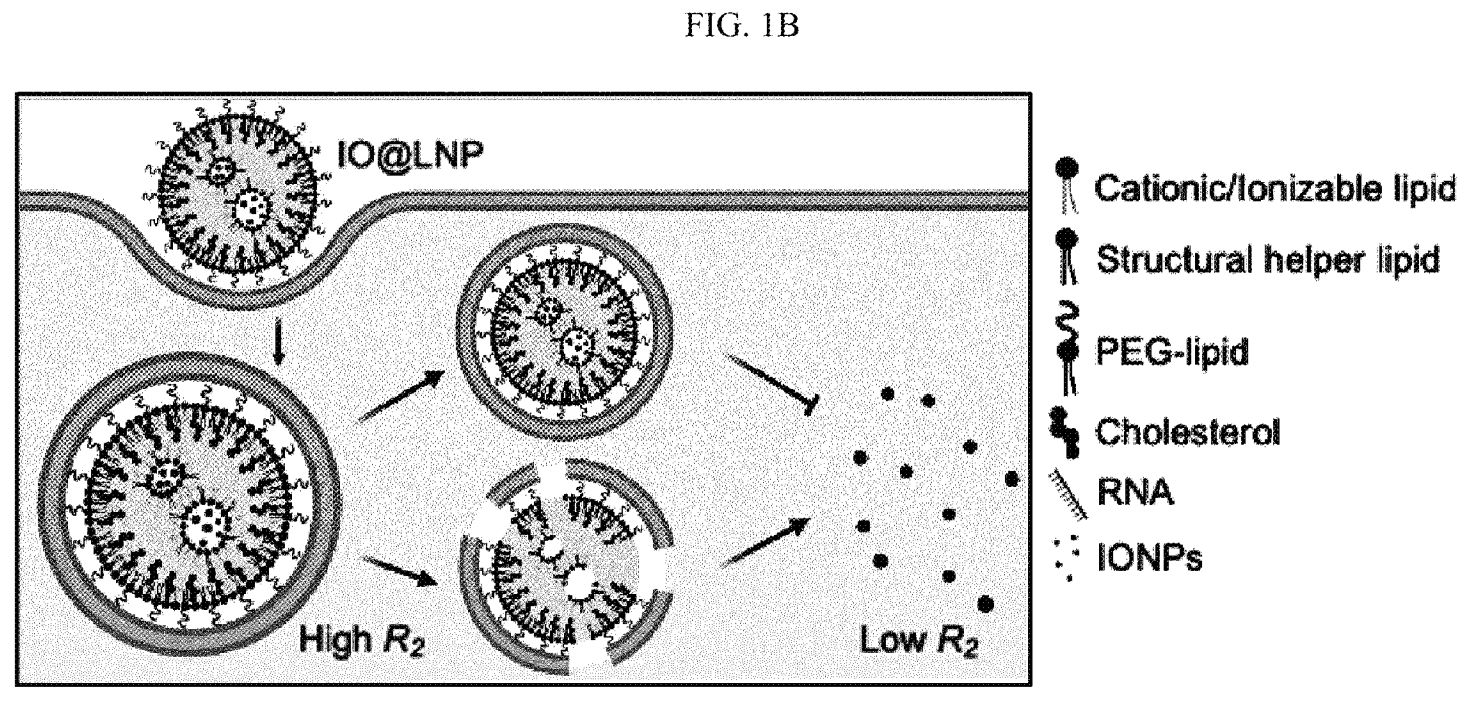

FIGS. 1A and 1B schematically illustrate an endosomal escape process of drug delivery particles loaded with RNAs or iron oxides.

Figure 2B:
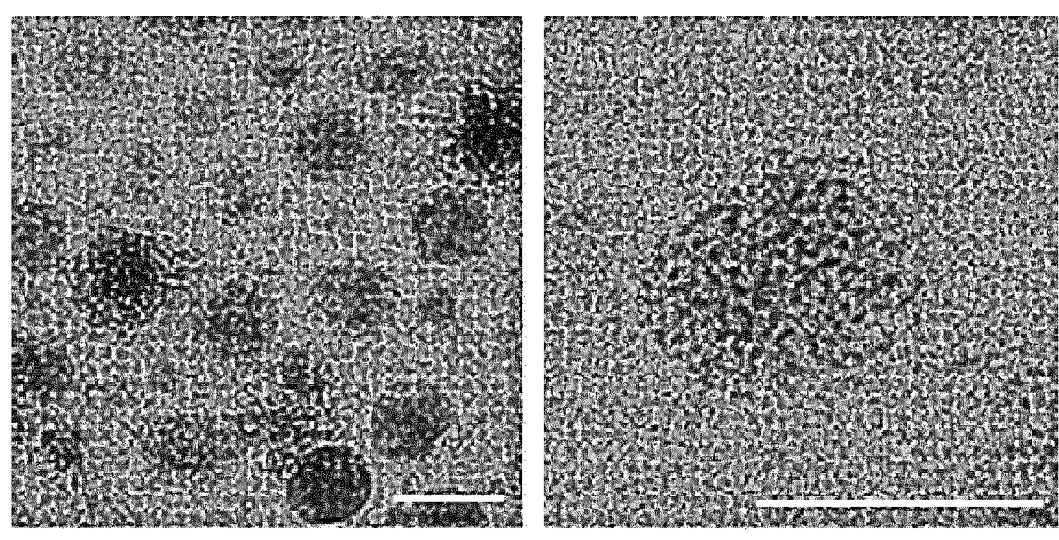
Figure 2C:
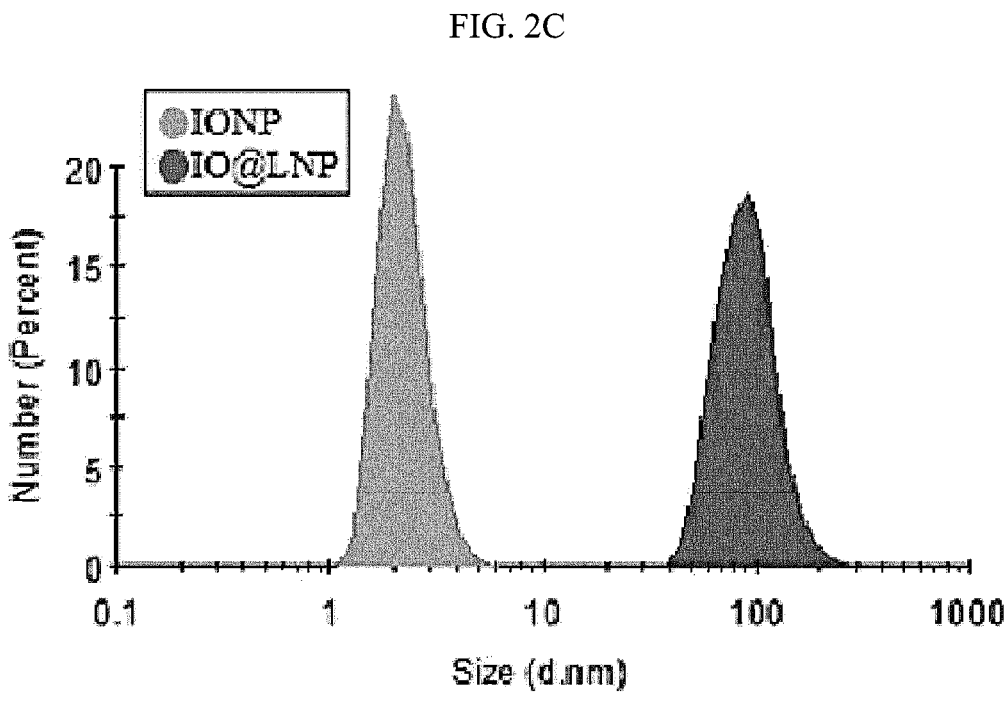
Figure 2D:
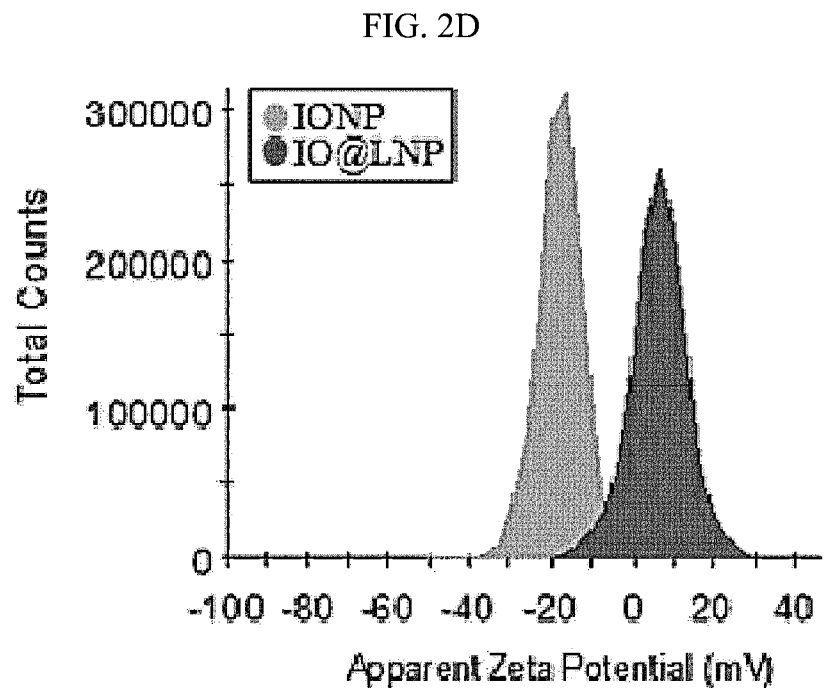
Figure 2E:
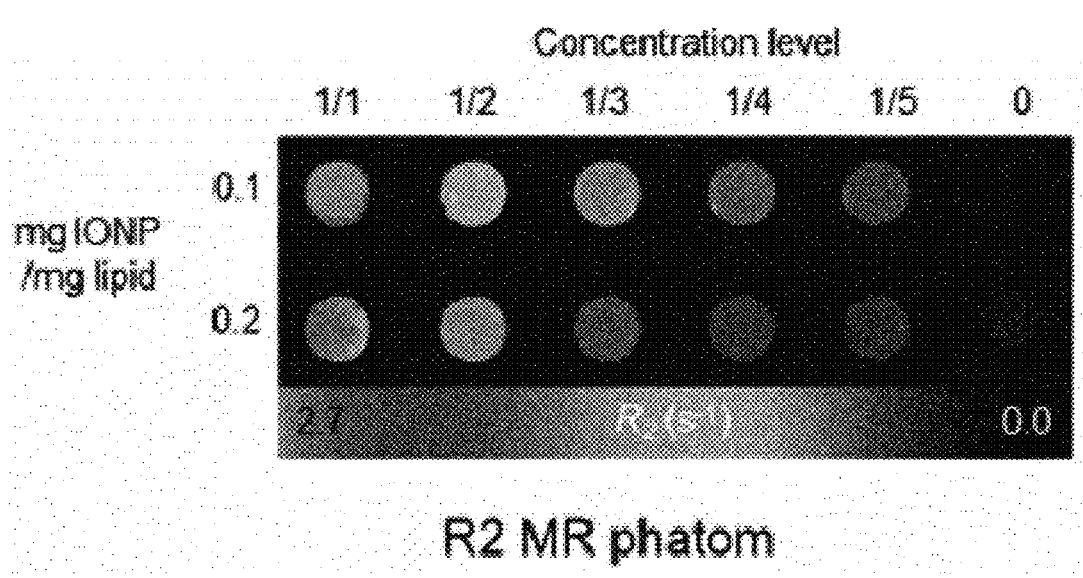
Figure 2F:
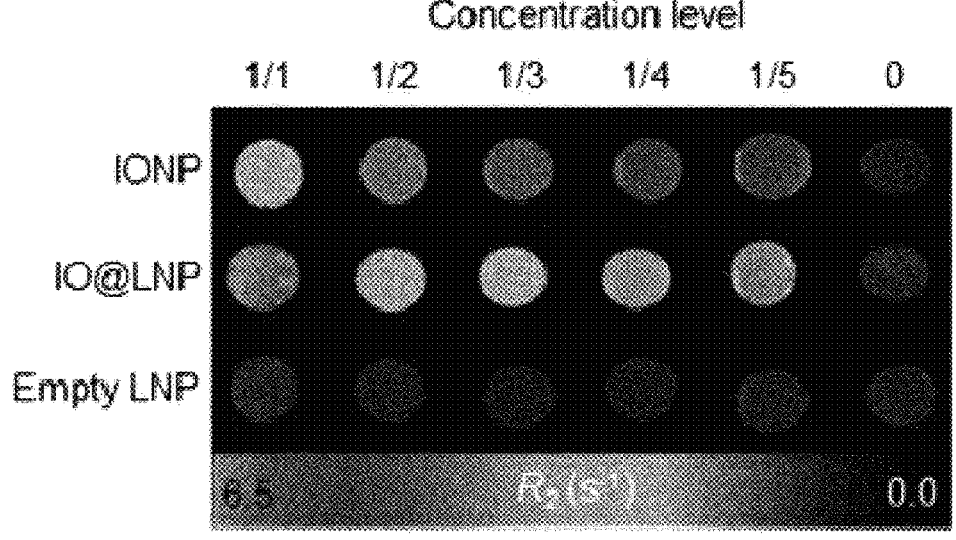
Figure 2G:
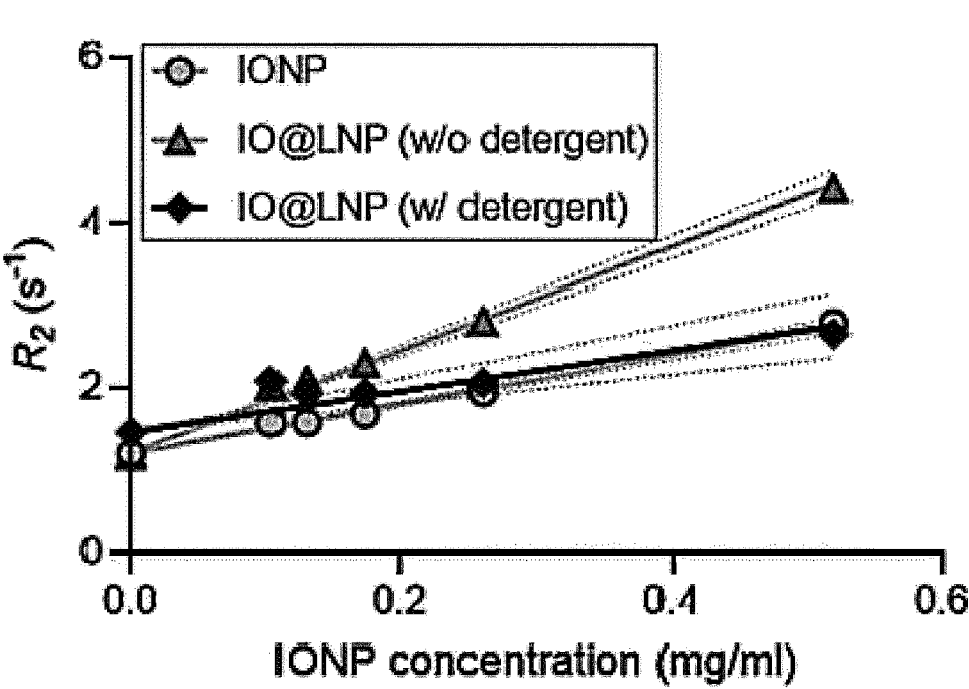
Figure 2H:
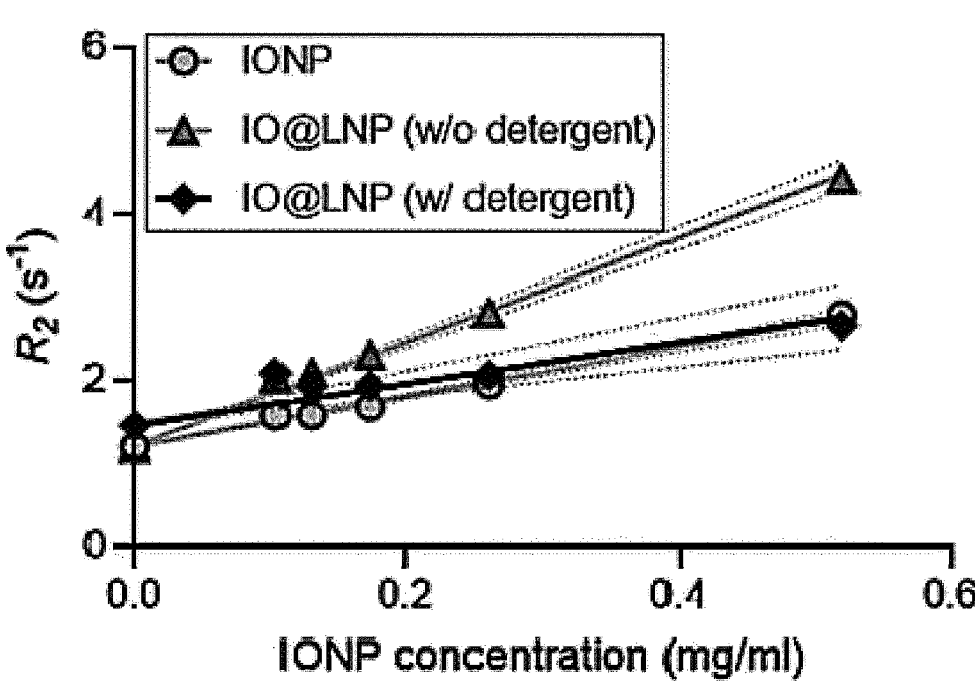

FIGS. 2A to 2H illustrate physicochemical properties of iron oxide nanoparticles (IONPs) and iron oxide-loaded lipid nanoparticles (IO@LNP). Specifically, FIG. 2A is representative transmission electron microscopy (TEM) images showing ultrasmall and monodisperse IONPs (black dots) synthesized by solvothermal synthesis (scale bar=20 nm); FIG. 2B is representative cryo-TEM images of IO@LNP (0.2 mg IONP/mg lipid) (black dots of LNPs represent IONPs, scale bar=100 nm); FIG. 2C illustrates a hydrodynamic size distribution of IONPs and IO@LNPs; FIG. 2D illustrates a zeta potential distribution of IONPs and IO@LNPs, wherein IO@LNP have larger amounts of positive surface charges (6.11±7.18 mV) than those of negatively charged IONPs (−17.7±5.09) due to cationic lipids; FIG. 2E illustrates an MR phantom $R_2$ map image of IO@LNP according to a ratio of IONPs (mg) to lipids (mg); FIG. 2F illustrates an MR phantom $R_2$ map image of IONP, IO@LNP and empty LNP, wherein these images are obtained by performing serial dilutions from 1/1 (0.87 mg IONP and 0 mg total lipid per ml for IONP, 0.87 mg IONP and 4.33 mg total lipid per ml for IO@LNP, and 0 mg IONP and 4.33 mg total lipid per ml for empty LNP) to 1/5 in concentration levels, and a saline sample was represented as 0; FIG. 2G illustrates $R_2$ magnetic relaxation rate values according to the concentration of free iron oxides (IONP, brown, y=2.18x+1.05, $R_2$=0.99) and iron oxides loaded in lipid nanoparticles (IONP in IO@LNP, red, y=5.69x+1.05, $R_2$=0.99), wherein each dotted line area represents the 95% confidence interval of each regression curve; and FIG. 2H illustrates $R_2$ magnetic relaxation rate values according to whether or not Triton X-100 detergent was treated in IO@LNP, and specifically illustrates $R_2$ magnetic relaxation rate values of free iron oxides (IONP, brown, y=1.79x+1.72, $R_2$=0.94), iron oxides loaded in lipid nanoparticles not treated with detergent (IO@LNP (w/o detergent), red, y=6.0x+1.33, $R_2$=1.00) and iron oxides loaded in lipid nanoparticles treated with detergent (IO@LNP (w/detergent, blue, y=1.25x+1.74, $R_2$=0.78)), wherein each dotted line area represents the 95% confidence interval for each regression curve.

Figure 3A:
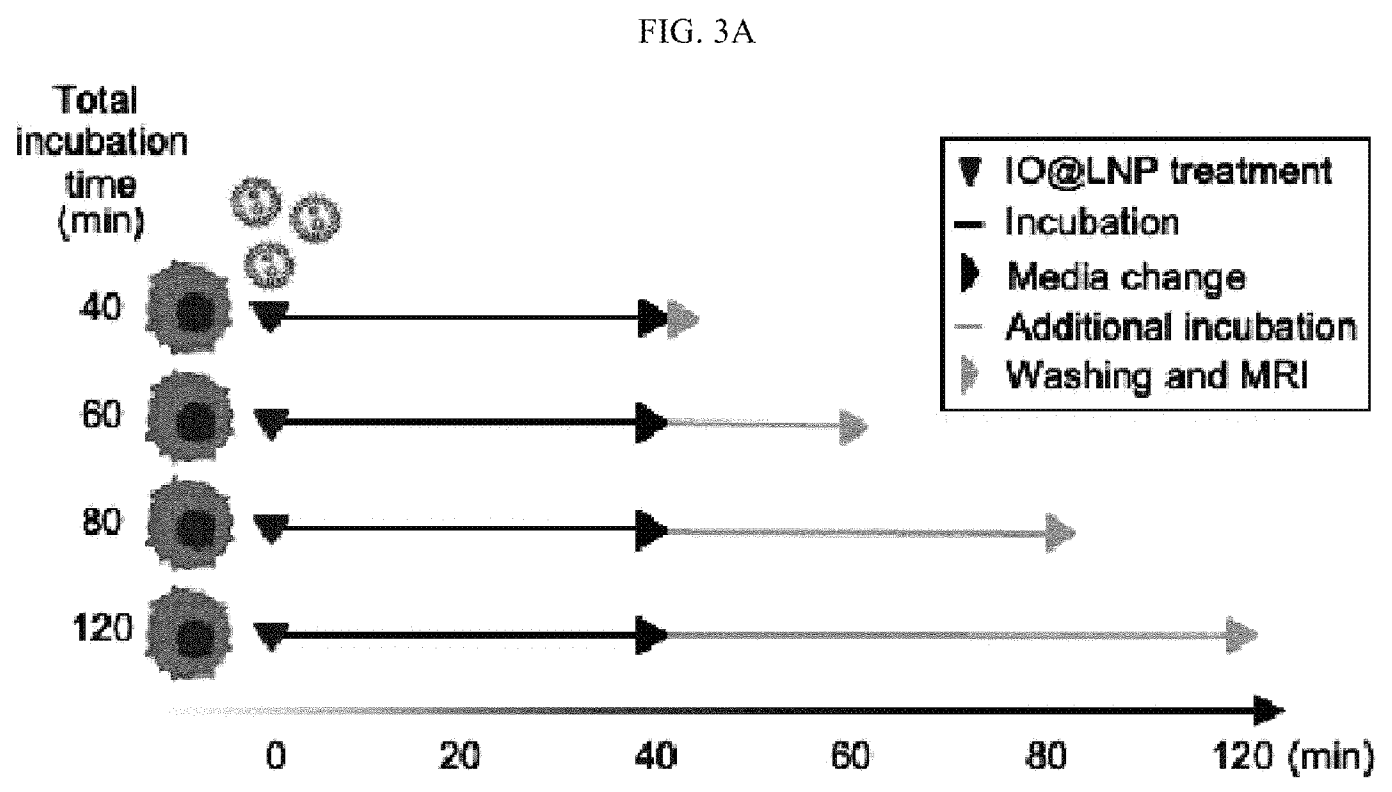
Figure 3B:
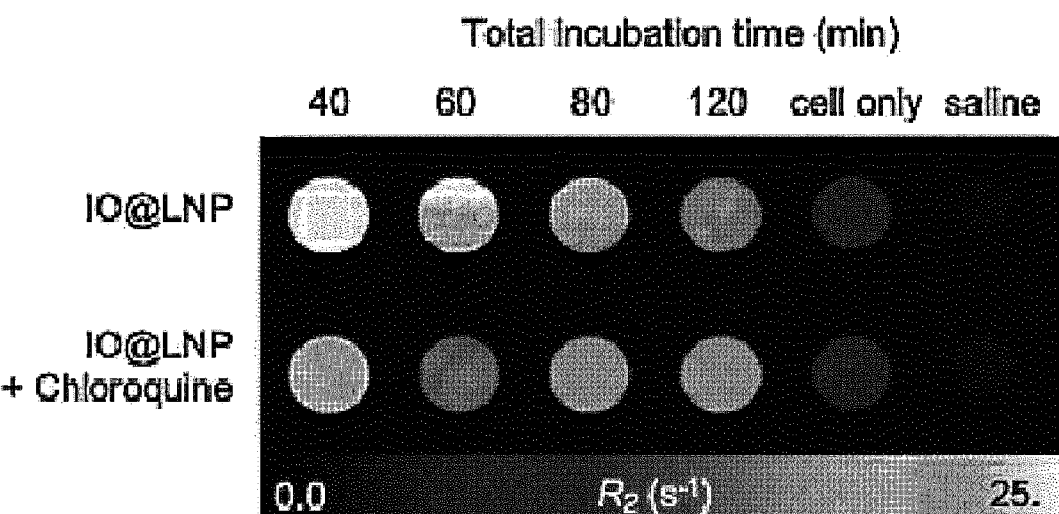
Figure 3C:
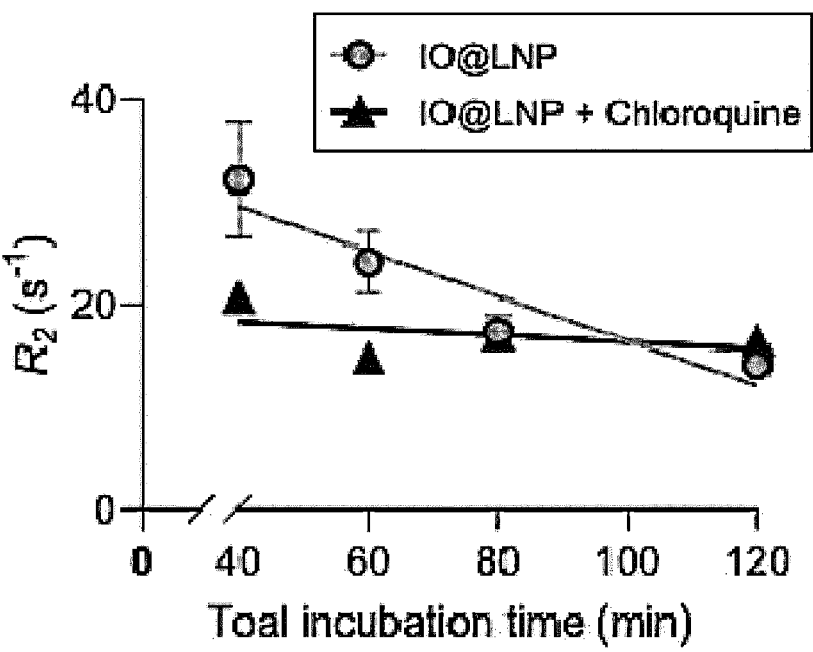

FIGS. 3A to 3C illustrate results of (in vitro) experiments on changes in $R_2$ magnetic relaxation rate due to a lapse of time after treating cells with iron oxide nanoparticle-loaded lipid nanoparticles. Specifically, FIG. 3A illustrates that IO@LNPs were incubated along with cells for LNP uptake time of the cells (40 minutes), and then further incubated for various time points (0, 20, 40 and 80 minutes). Finally, each harvested cell ($1.0×10^7$ to $1.9×10^7$ total cells/ml; cell survival rate (cell viability): 74%-87%) was fixed with 4% paraformaldehyde (PFA); FIG. 3B illustrates an in vitro MR phantom $R_2$ map image of the cell pellets obtained from FIG. 3A; and FIG. 3C illustrates changes in $R_2$ magnetic relaxation rate value in a group (y=−0.03x+19.64, $R_2$=0.2147) treated with chloroquine which promotes endosomal escape.

Figure 4A:
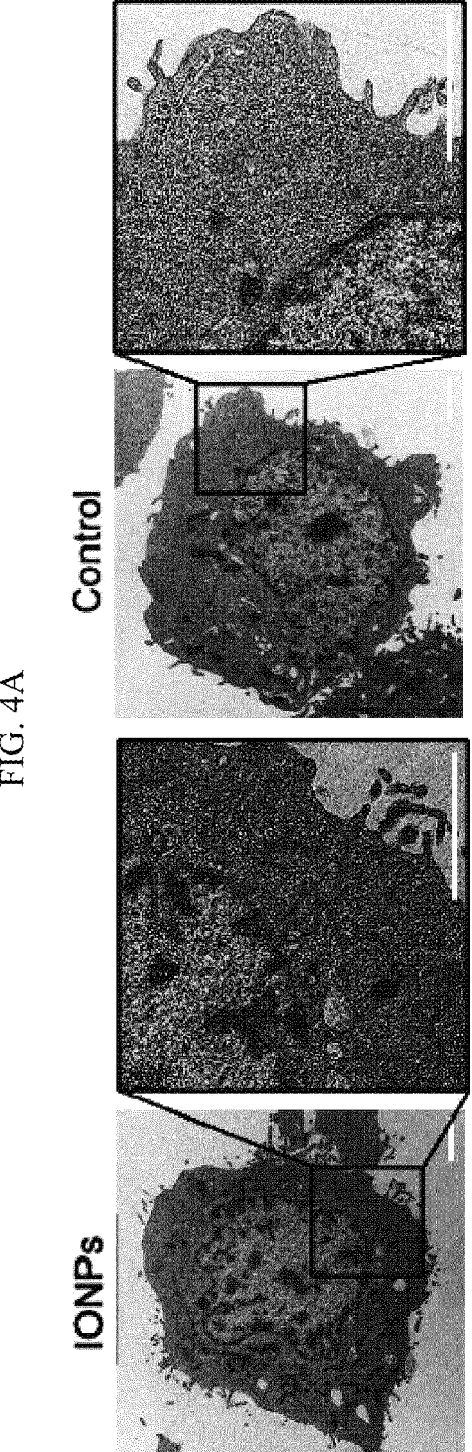
Figure 4B:
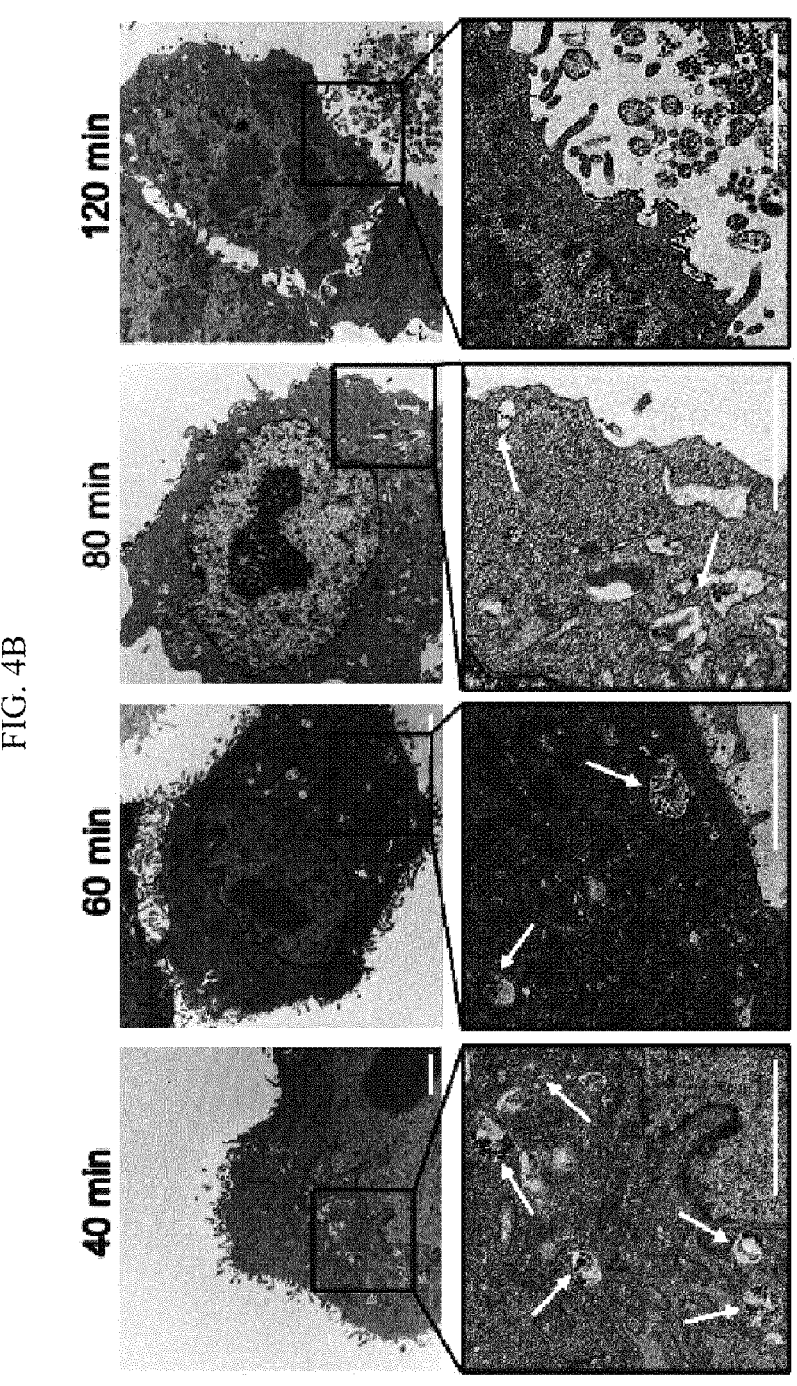
Figure 4C:
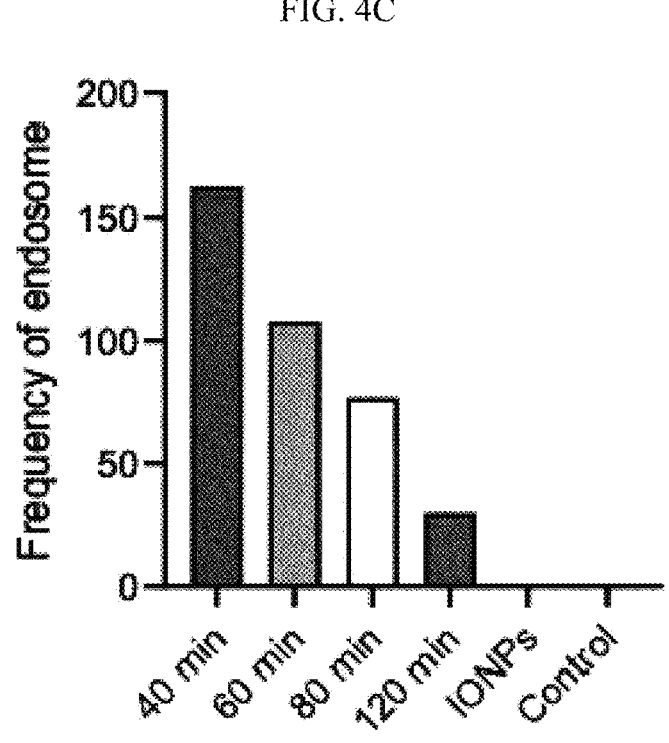
Figure 4D:
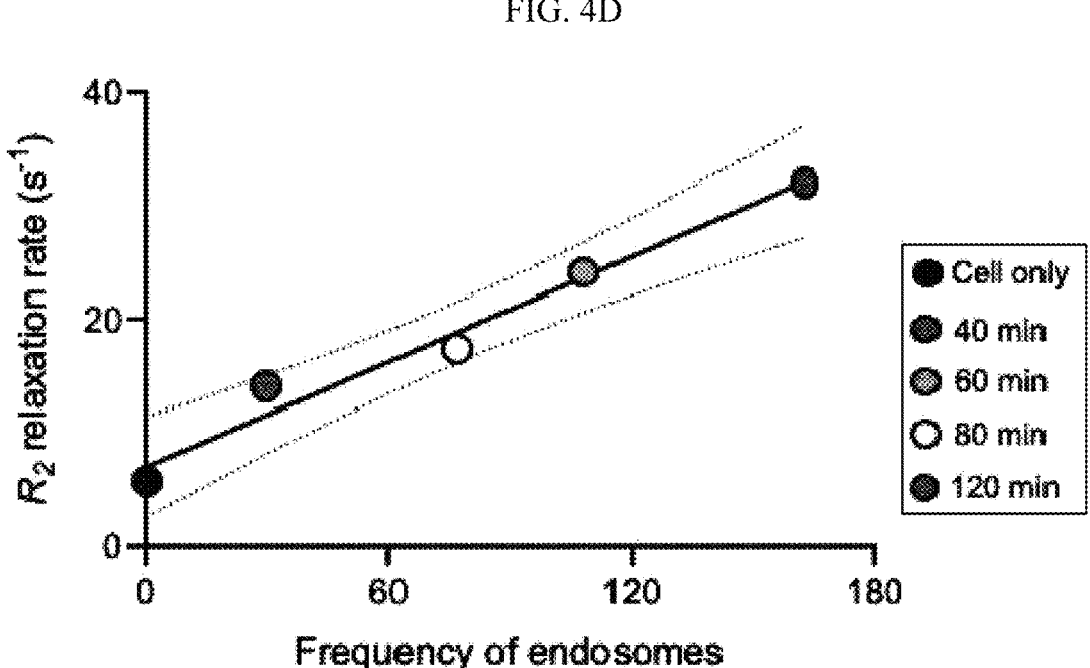

FIGS. 4A to 4D illustrate a correlation between Bio-TEM and in vitro MRI results. Specifically, FIG. 4A is Bio-TEM images (n=20 images per group) of 4T1 cells treated with an excess amount of IONPs or without any treatment (Control), wherein no visible endosomes including black dots were observed in 4T1 cells treated with an excess amount of IONPs or without any treatment (Control); FIG. 4B is Bio-TEM images of 4T1 cells treated with IO@LNPs (n=20 images per group), wherein endosomes (arrows) were most abundantly detected at 40 minutes (scale bar=2 μm); FIG. 4C is results of semi-quantitative analysis on Bio-TEM results showing a sum of the number of endosomes in a region of 8 μm×8 μm per Bio-TEM image (n=20 images per group), wherein intracellular IO@LNPs were calculated only when the cavity had three or more black dots with clear contrast and a size of about 100-200 nm, and as a result, it was confirmed that the number of endosomes was decreased over time due to the endosomal escape; and FIG. 4D illustrates results of correlation analysis (y=0.23x+2.97, $R_2$=0.77) between Bio-TEM quantification and in vitro MRI results, wherein as the incubation time was increased, endosomal escape was increased and the $R_2$ relaxation rate was simultaneously decreased.

Figure 5A:
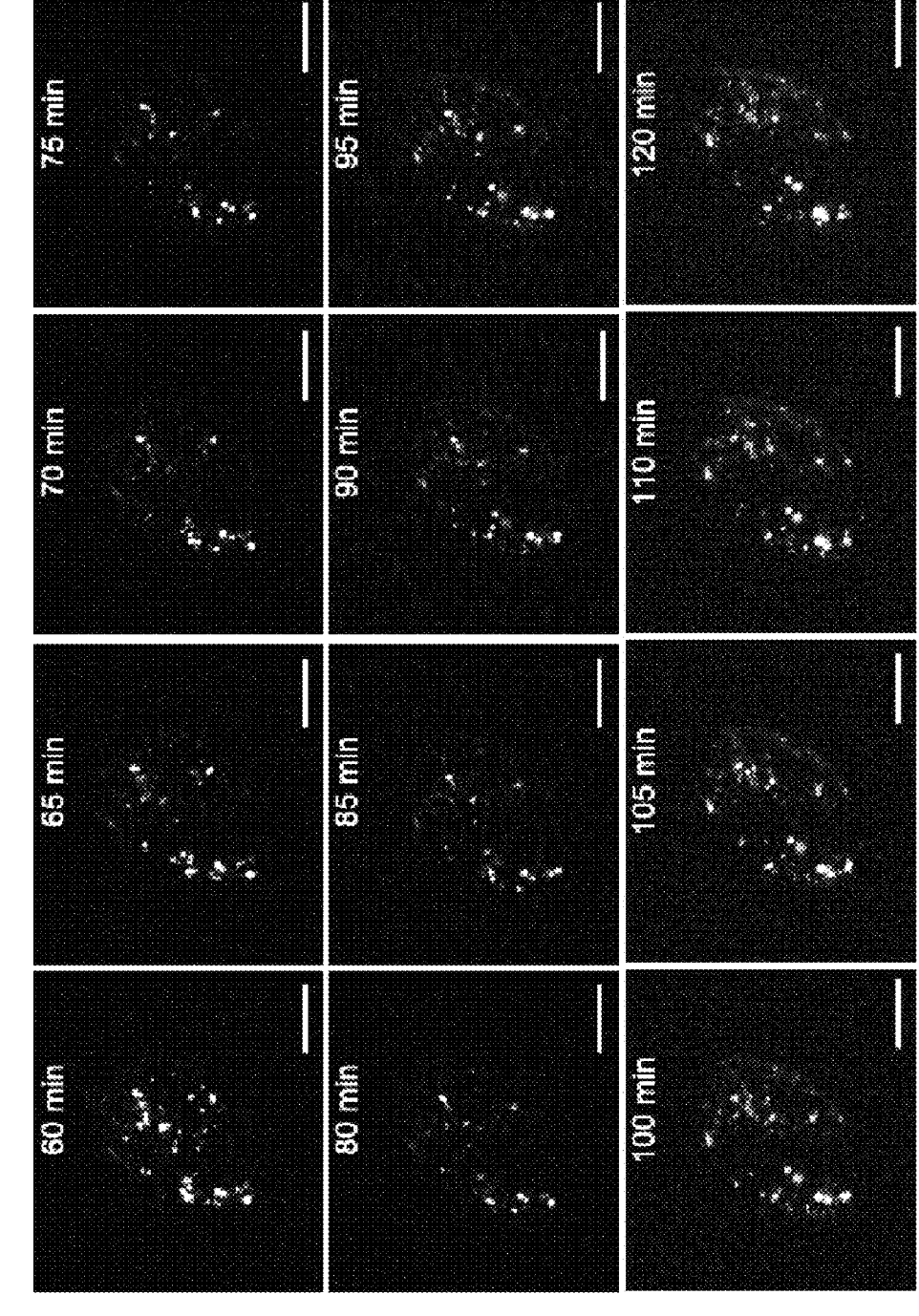
Figure 5B:
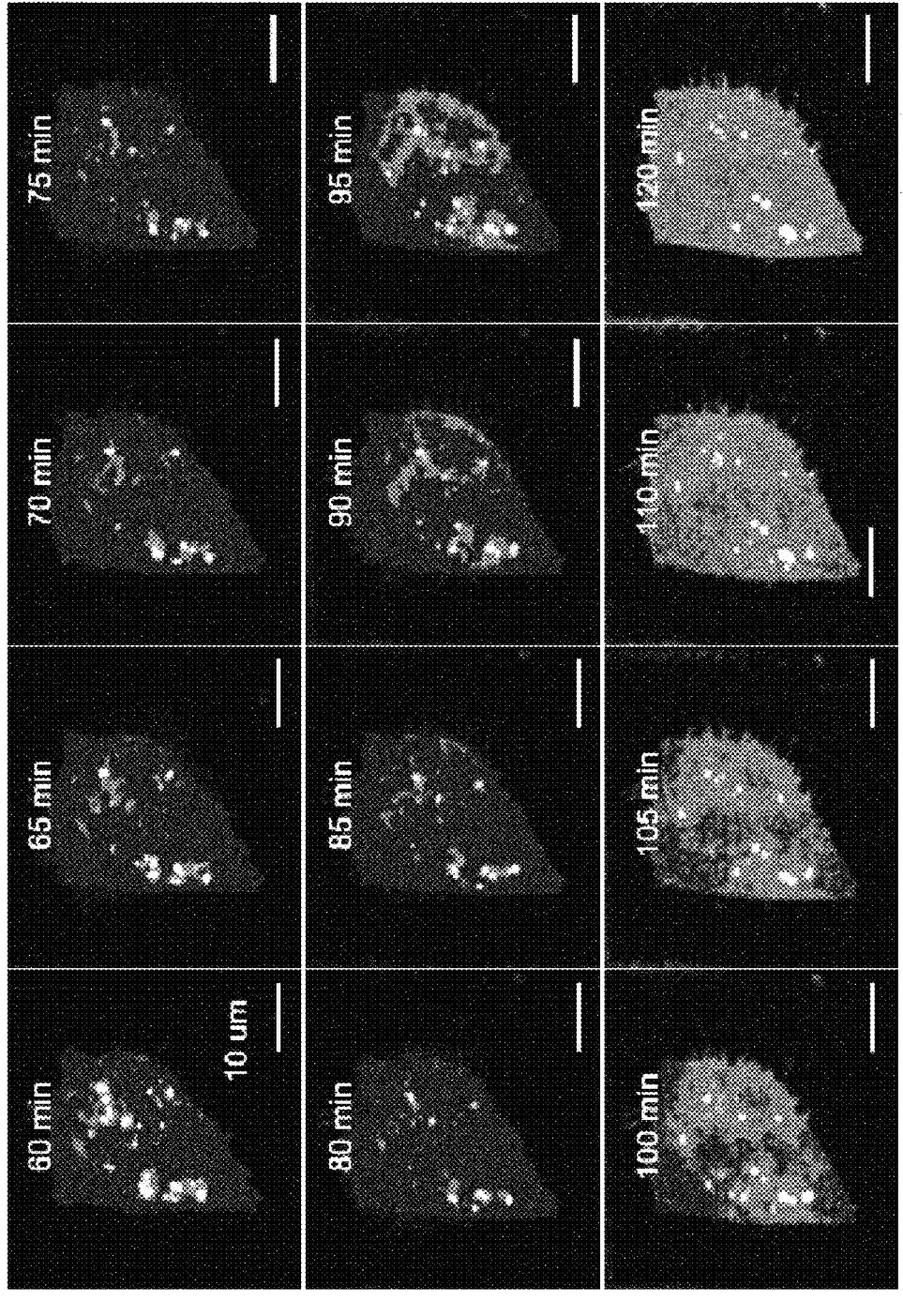
Figure 5C:
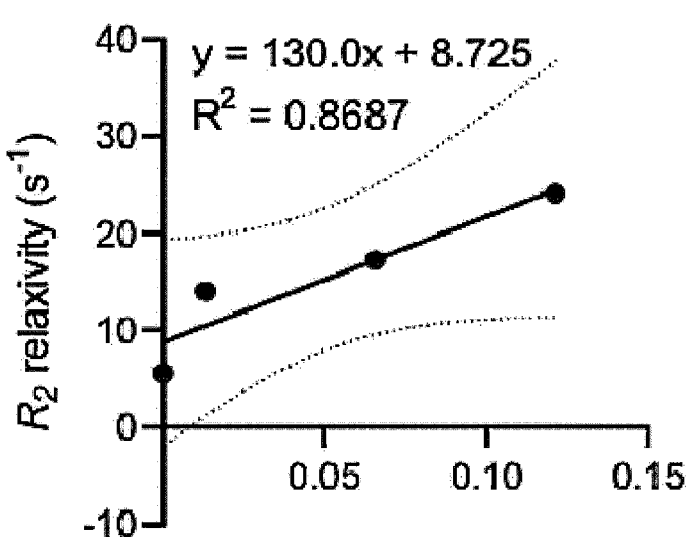
Figure 5D:
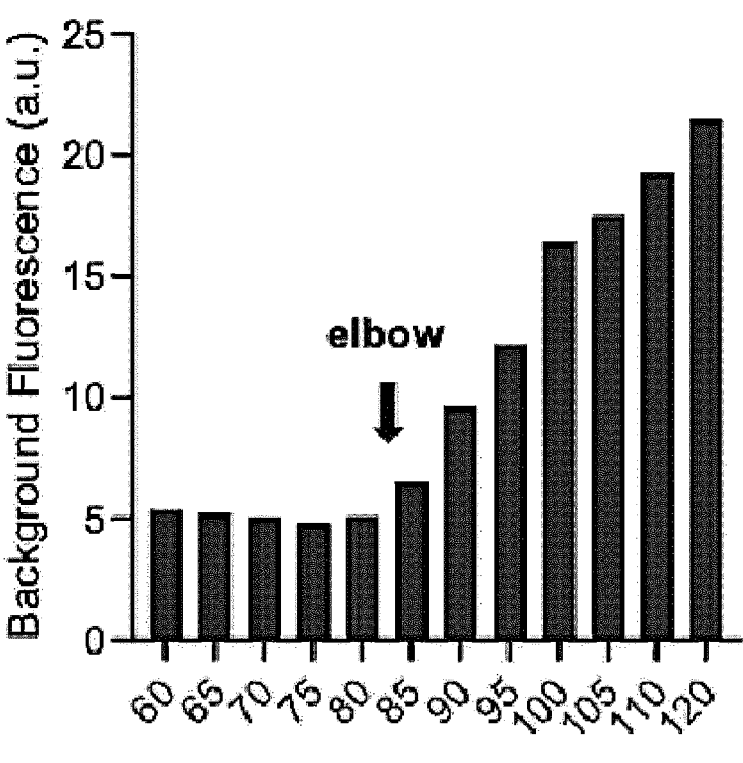

FIGS. 5A to 5D illustrate Tomocube imaging results of IO@LNP/Sulfo-cy5.5. Specifically, FIG. 5A is fluorescence images of IO@LNP/Sulfo-cy5.5 obtained from Tomocube every 5 minutes (scale bar=10 μm); FIG. 5B is fluorescence images of IO@LNP/Sulfo-cy5.5 classified into pixels brighter than the 95th percentile (yellow) and pixels brighter than the 60th percentile (green and yellow); FIG. 5C illustrates a linear relationship between the nominal number of vesicles and the $R_2$ value, wherein the nominal number of vesicles is defined as a value obtained by dividing the yellow area by the green area; and FIG. 5D illustrates results of quantitative analysis on extracellular fluorescence intensity from IO@LNP/Sulfo-cy5.5, wherein an elbow point was seen after 80 minutes, thereby indicating that active exocytosis occurred after 80 minutes.

Figure 6A:
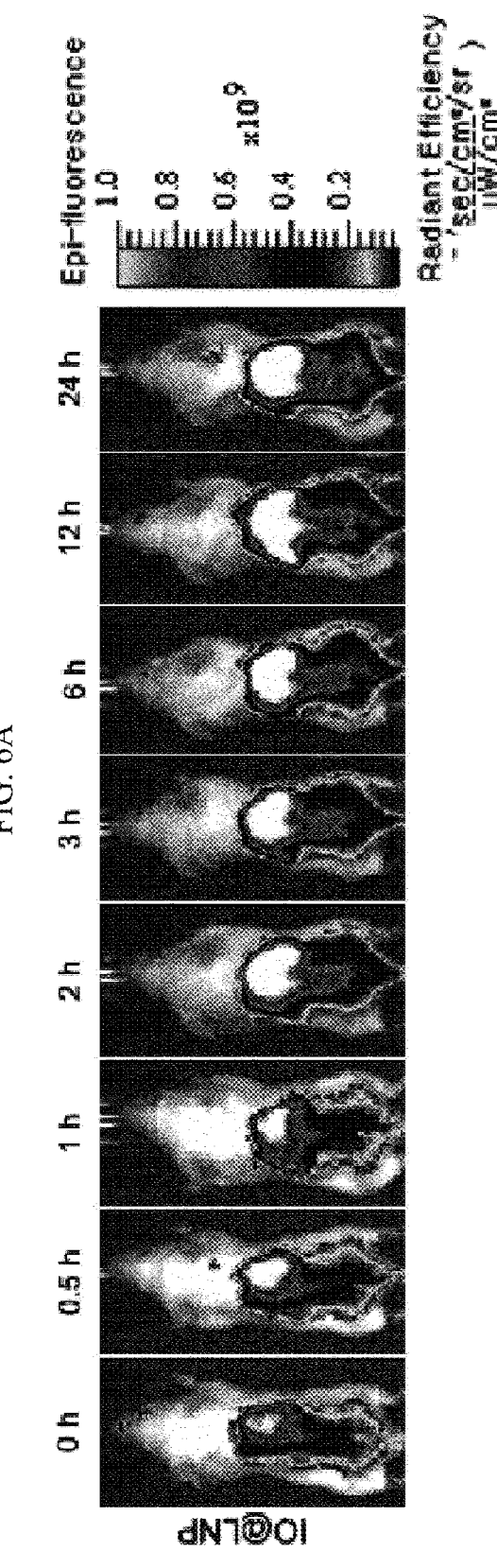
Figure 6B:
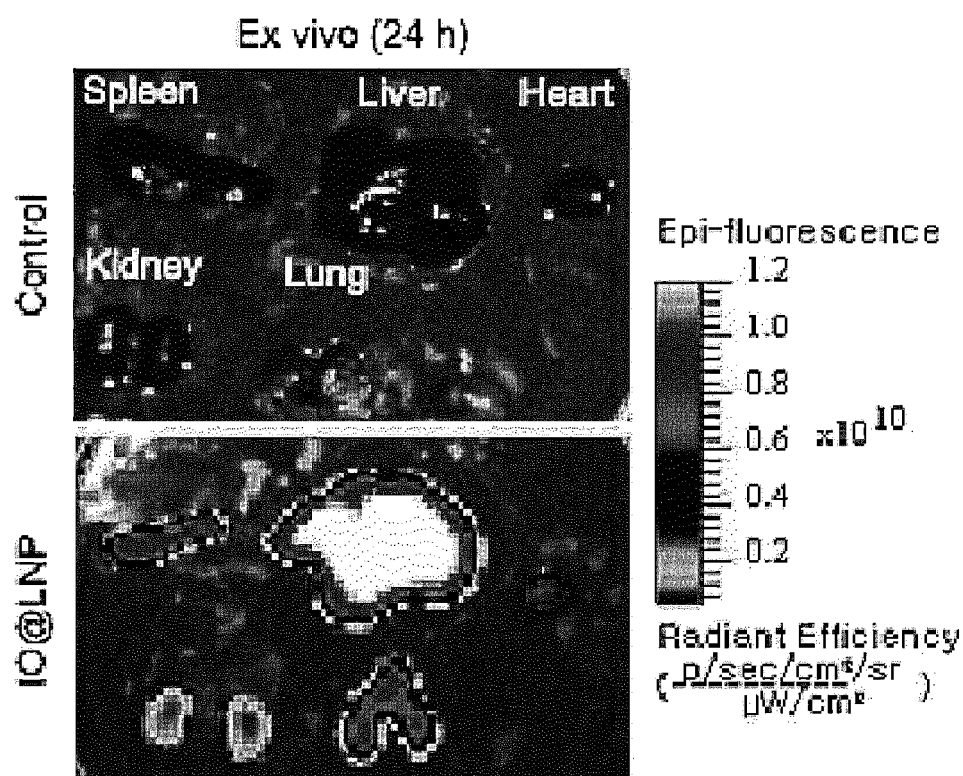
Figure 6C:
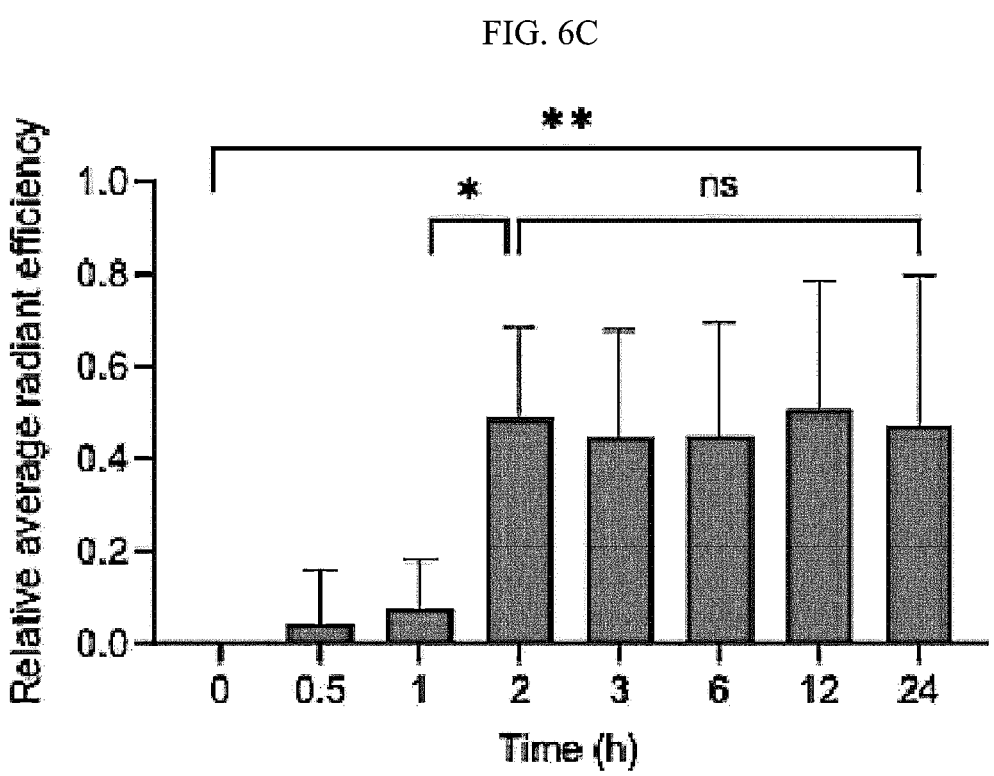
Figure 6D:
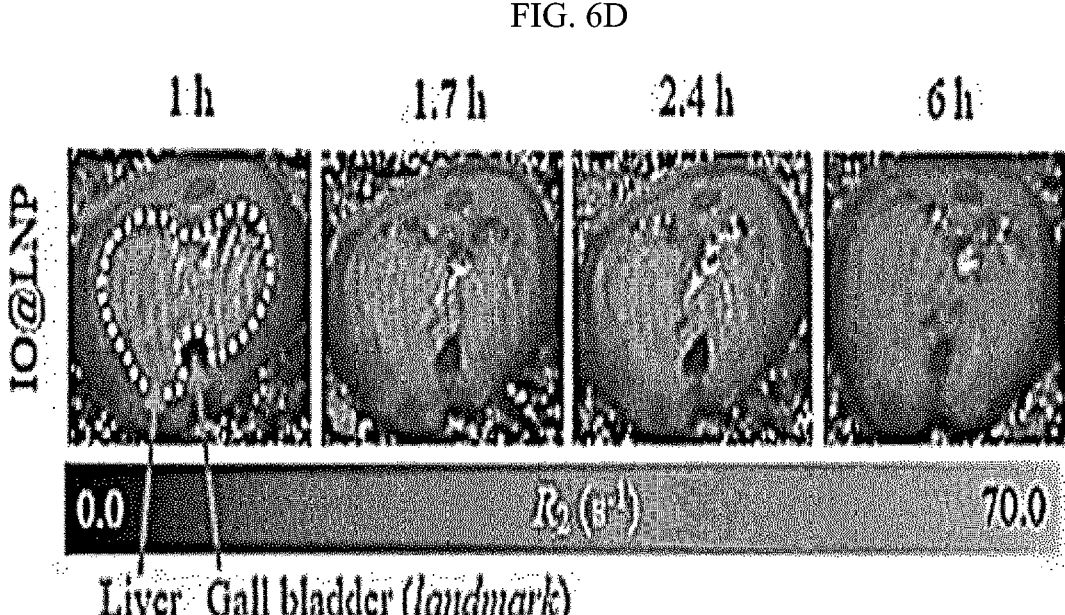
Figures 6E, 7A:
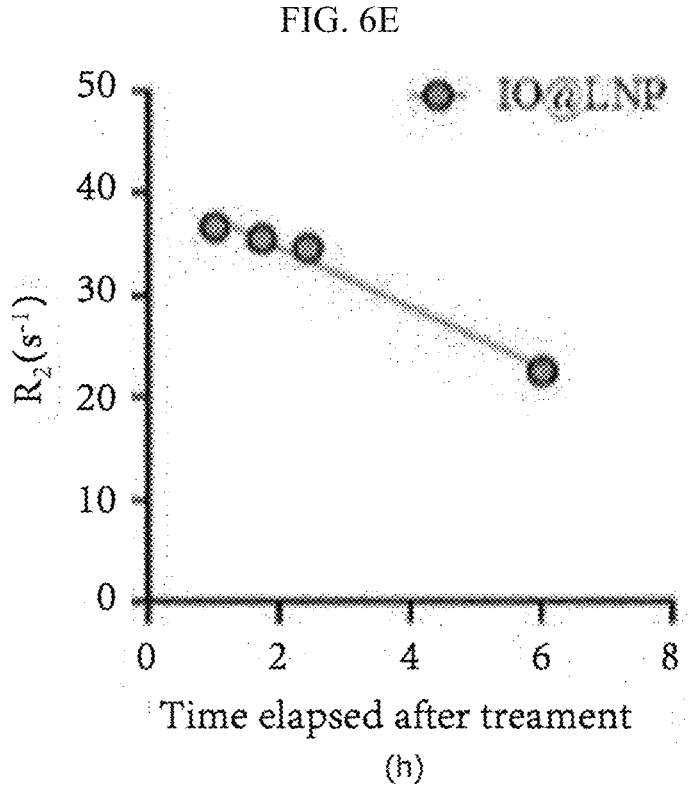

FIGS. 6A to 6E illustrate results of in vivo experiments on changes in liver $R_2$ magnetic relaxation rate due to a lapse of time after treating a mouse with iron oxide nanoparticle-loaded lipid nanoparticles. Specifically, FIG. 6A is images by visualizing an in vivo imaging system (IVIS) of mouse intravenously injected with IO@LNP/DIR, wherein the mouse was imaged after intravenous injection of IO@LNP compared to saline-treated control (n=4 Balb/c mice); FIG. 6B is fluorescence images showing major organs (spleen, liver, heart, kidney and lung) detected after 24 hours, wherein the fluorescence signal of the liver was detected significantly compared to other organs; FIG. 6C illustrates in vivo liver quantitative analysis results from FIG. 6A, wherein a region of interest (ROI) was allocated to the IVIS software to measure liver signals, and it was shown that a significant amount of IO@LNP reached the liver 2 hours after injection; FIG. 6D illustrates in vivo $R_2$ map images of mouse liver at different time points after treatment with IO@LNPs (0.8 mg IONP/4 mg total lipid/ml PBS). In contrast to the distribution of saturated LNPs in the liver after 2 hours, there was a region of mouse liver tissue showing a decrease in $R_2$ value, and through this, it can be seen that endosomal escape occurred in the corresponding region; and FIG. 6E illustrates $R_2$ magnetic relaxation rates due to a lapse of time after treating with IO@LNPs, wherein IO@LNPs-treated mice exhibited a linear decrease in $R_2$ magnetic relaxation rate, and it can be seen that release of IONPs at a predetermined rate occurred in IO@LNPs due to the endosomal escape.

Figure 7B:
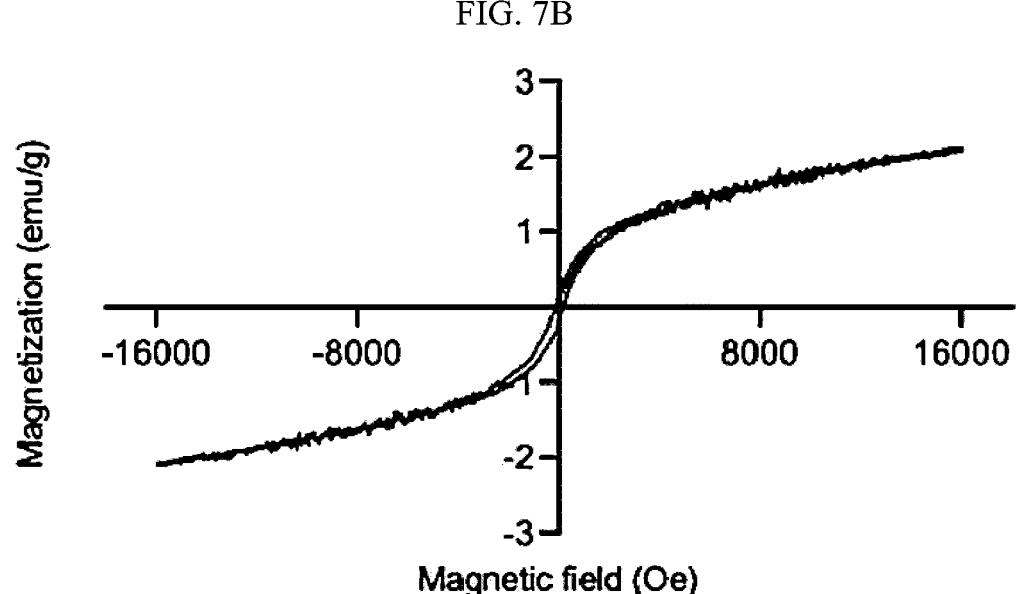

FIGS. 7A and 7B illustrate FT-IR and VSM results of iron oxides. Specifically, FIG. 7A is Fourier transform infrared spectroscopy (FTIR) spectrum results of IONPs; and FIG. 7B is a normalized field-dependent magnetization curve (M-H curve) of IONPs determined by a vibrating sample magnetometer at 300 K, wherein the normalized saturation moment of IONPs is about 3 emu/g.

Figures 8A, 8B:
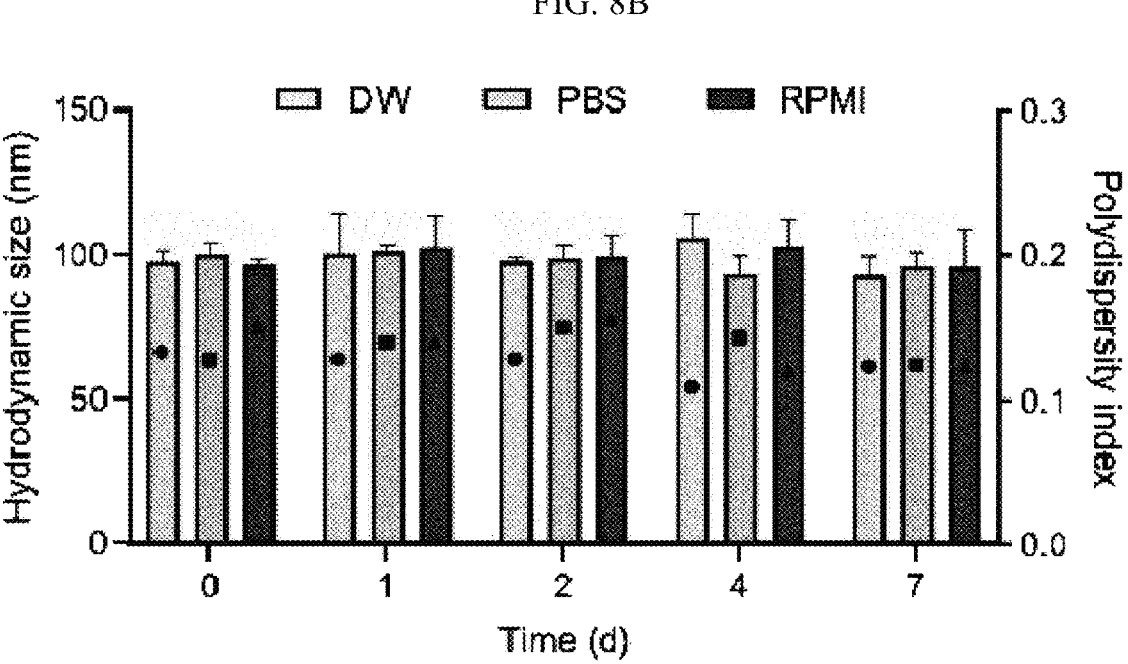
Figure 8C:
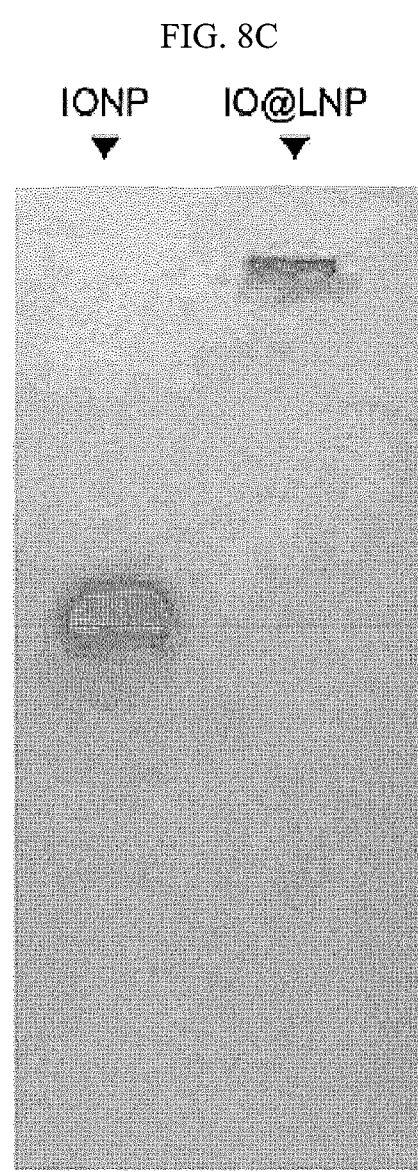

FIGS. 8A to 8C illustrate diameters and polydispersity index (PDI) of IONPs and IO@LNPs in various solvents over time measured by DLS. Specifically, FIG. 8A is stability test results of IONPs; FIG. 8B is stability test results of IO@LNPs; and FIG. 8C is electrophoresis results for IONPs and IO@LNPs.

Figure 9A:
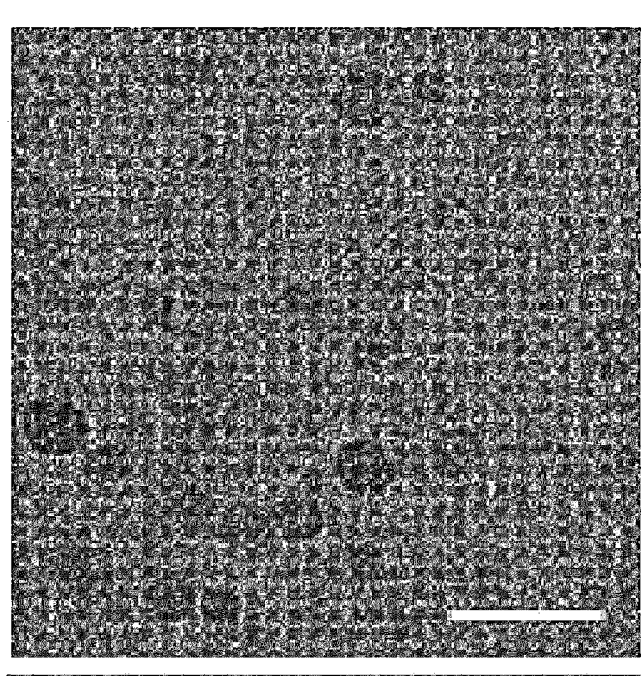
Figure 9A:
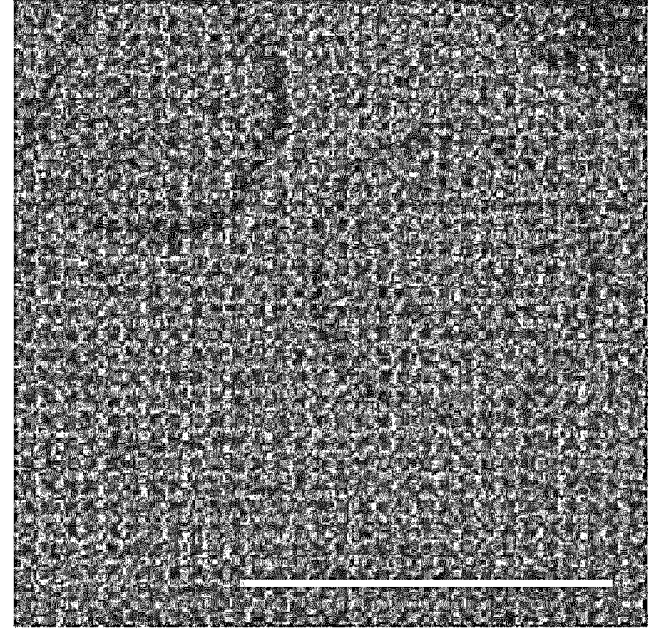
Figure 9B:
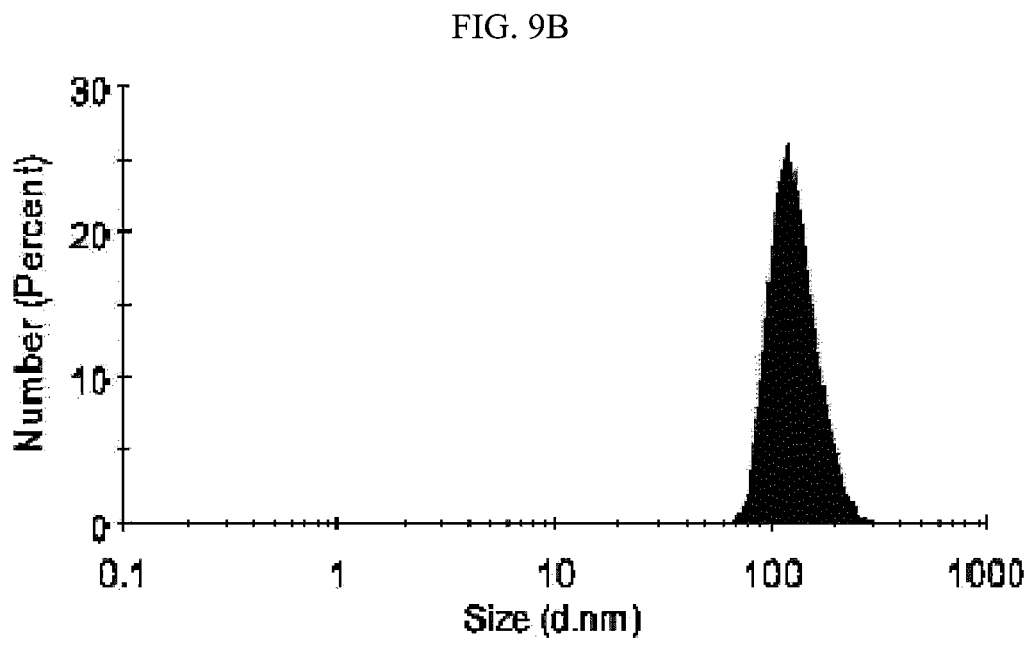
Figure 9C:
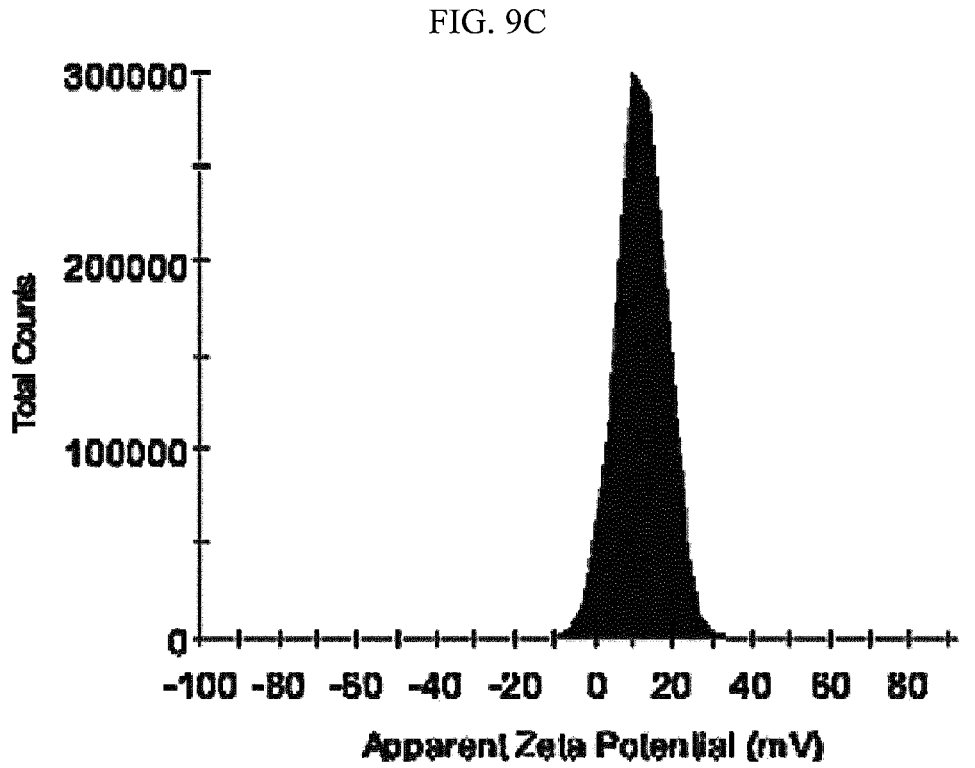

FIGS. 9A to 9C illustrate physicochemical properties of empty LNPs (Empty LNP). Specifically, FIG. 9A is representative transmission electron microscopy (TEM) images (scale bar=100 nm) of empty LNPs which do not contain IONPs; FIG. 9B is a hydrodynamic size distribution of empty LNPs showing diameters of 129.7±31.18 nm (mean±SD) and a PDI of 0.040; and FIG. 9C is a zeta potential distribution of empty LNPs (11.9±6.01 mV), which are more negatively charged than IO@LNPs (6.11±7.18 mV).

Figure 10A:
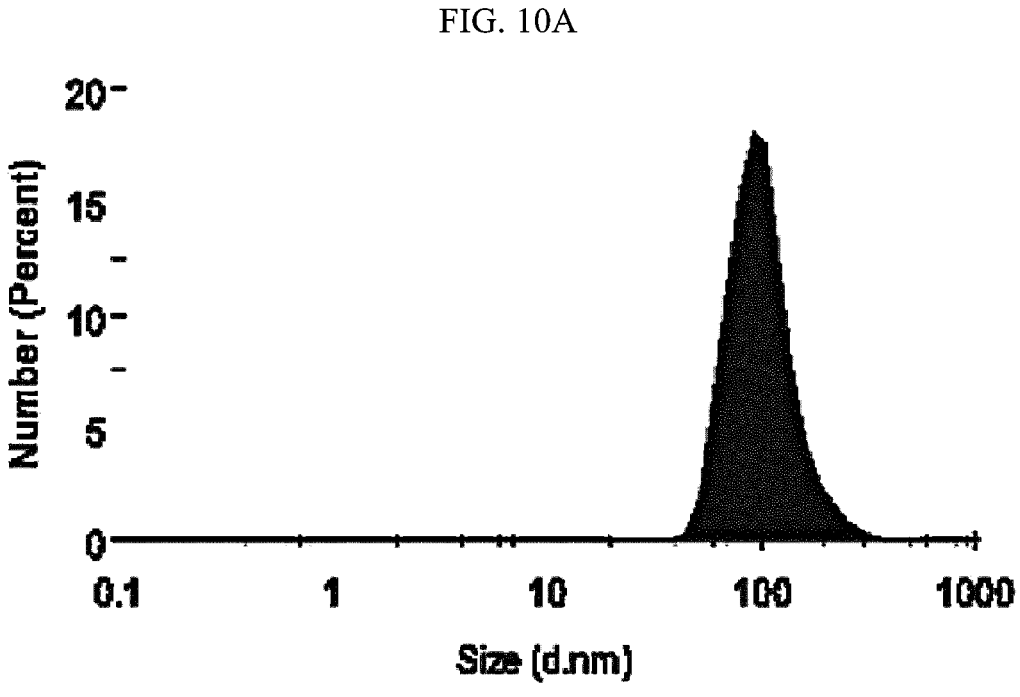
Figure 10B:
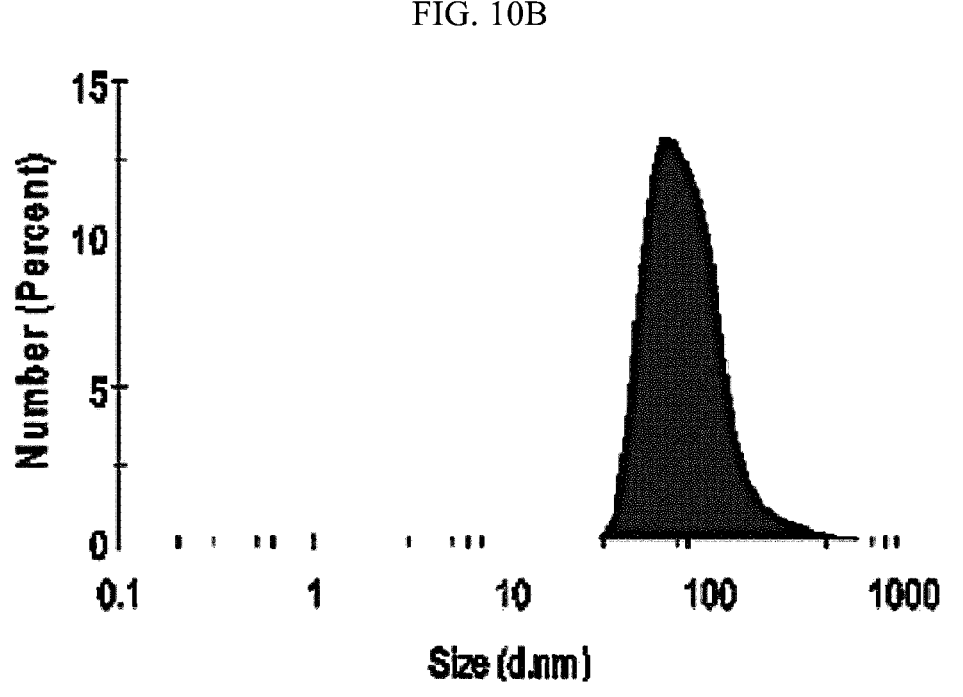

FIGS. 10A and 10B illustrate physicochemical properties of IO@LNPs labeled with a fluorescent dye (DiD, Sulfo-Cy5.5 amine). Specifically, FIG. 10A represents diameters (105.2±41.21 nm) and PDI (0.155) of IO@LNPs on which DiD, one of the fluorescent lipophilic dyes, was labeled on the surface; and FIG. 10B illustrates diameters (84.34±51.08 nm) and PDI (0.275) of IO@LNPs loaded with sulfo-Cy5.5 amine, one of the fluorescent hydrophilic dyes.

Figure 11A:
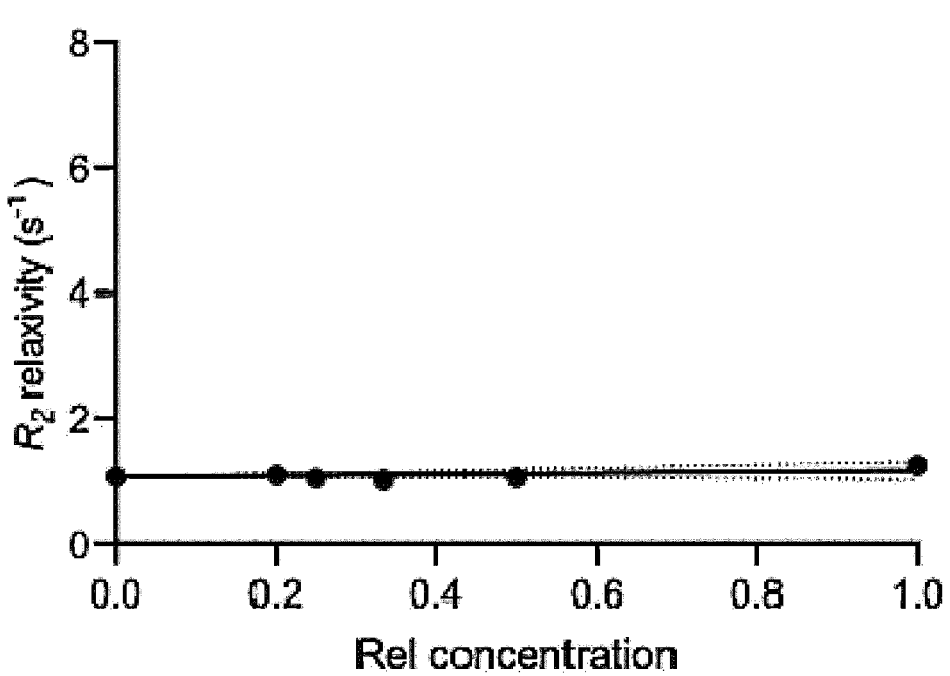
Figure 11B:
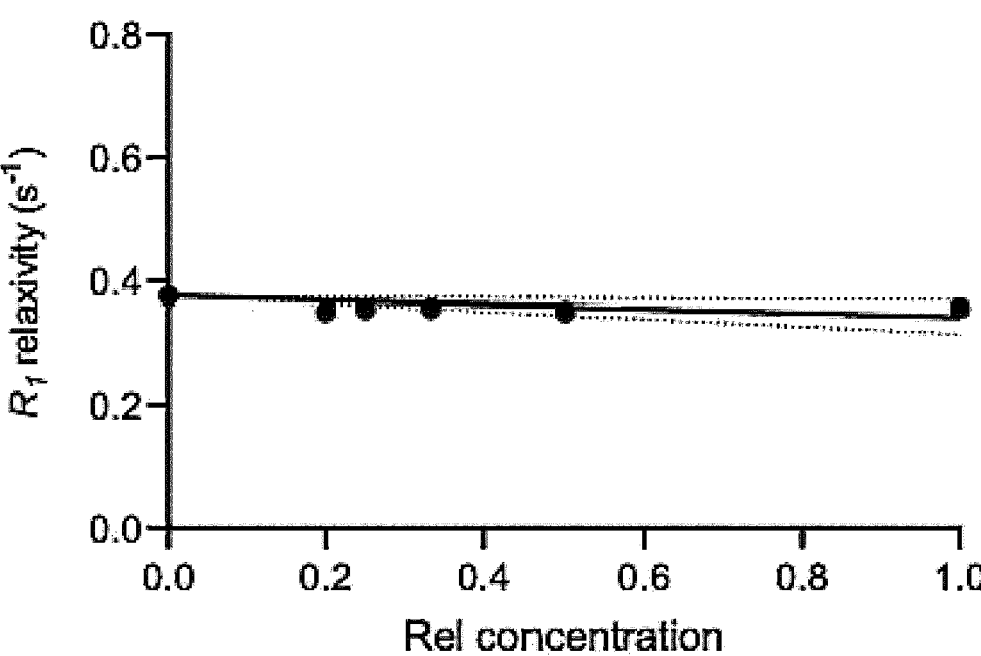

FIGS. 11A and 11B illustrate MR phantom results of empty LNPs. Specifically, FIG. 11A illustrates $R_2$ relaxation rate coefficient value (y=0.10x+0.75, $R_2$=0.42) of the empty LNPs; and FIG. 11B represents $R_1$ relaxation rate coefficient value (y=−0.03x+0.38, $R_2$=0.67) of the empty LNPs, wherein each dotted line area represents the 95% confidence interval for each regression curve.

Figure 12A:
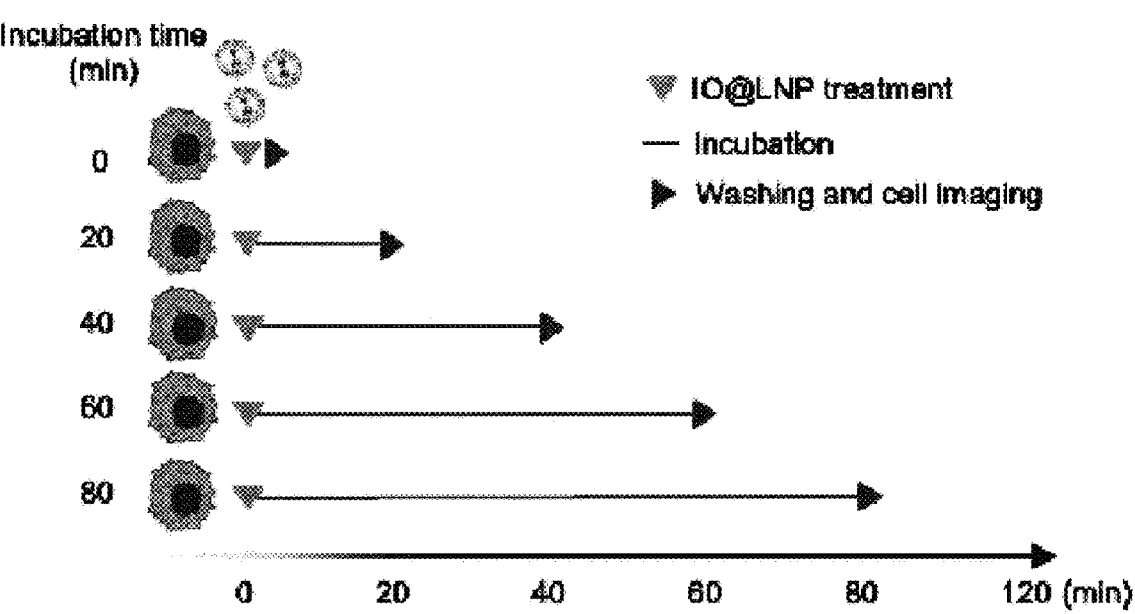
Figure 12B:
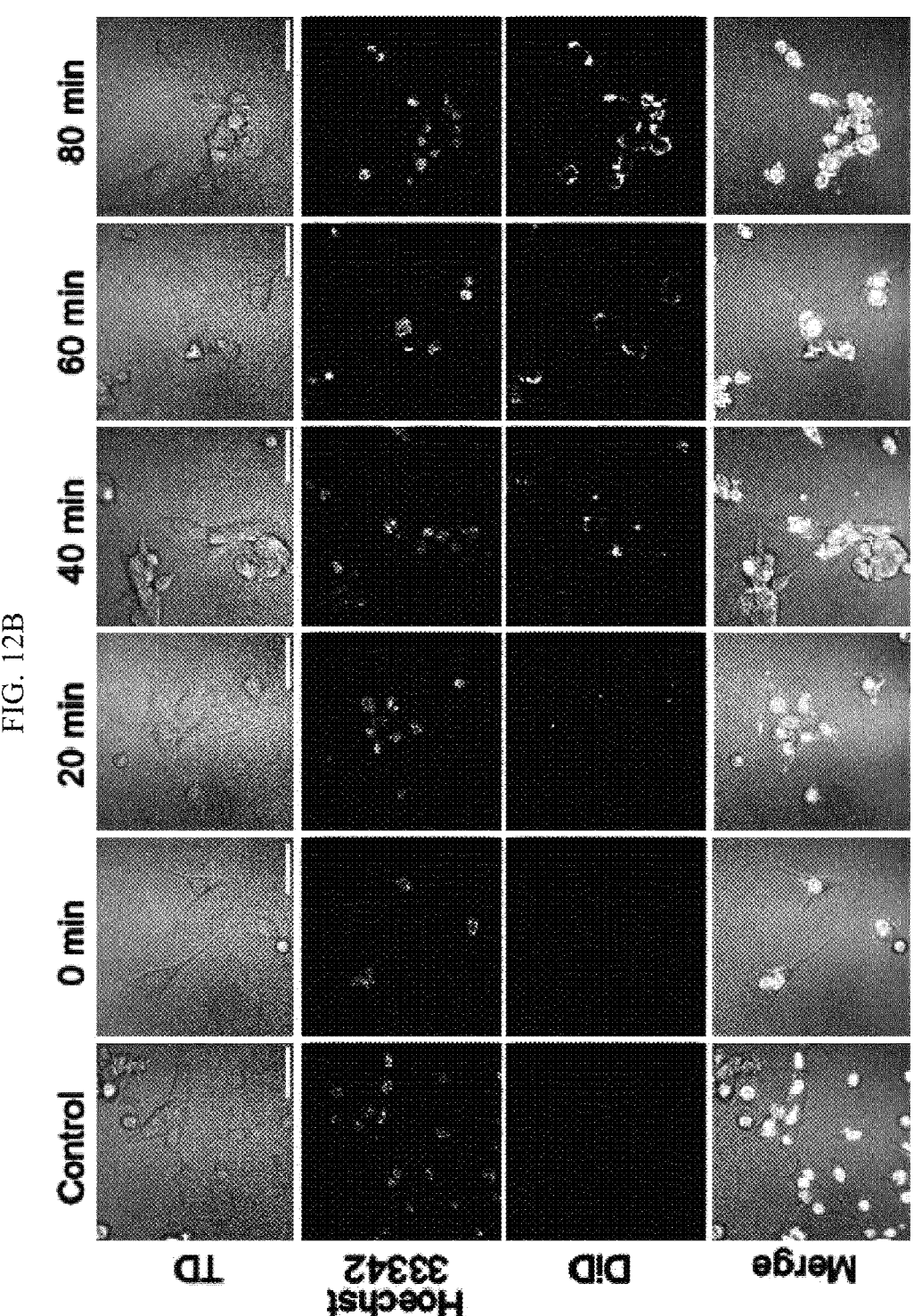

FIGS. 12A and 12B illustrate a degree of IO@LNP uptake by cells over time after treating 4T1 cells with IO@LNPs. Specifically, FIG. 12A is an experiment schedule to determine a start point of endosomal escape after treating 4T1 cells with IO@LNPs, wherein the cells were cultured along with IO@LNP/DiD (yellow), washed after different incubation times (pink), and then imaged by laser scanning confocal microscope; and FIG. 12B is confocal fluorescence images showing the cellular uptake of IO@LNPs, wherein nuclei were stained with Hoechst 33342 (blue), and DiD (red) showed the intracellular distribution of LNPs. These confocal fluorescence images showed gradual internalization of IO@LNPs inside the cytoplasm over time. LNPs were located on the cell membrane surface at 20 minutes. From 40 minutes after the start of incubation, LNPs are distributed with high mobility in the cytoplasm, thereby suggesting that endosomal escape is being performed (scale bar=50 μm).

Figure 13A:
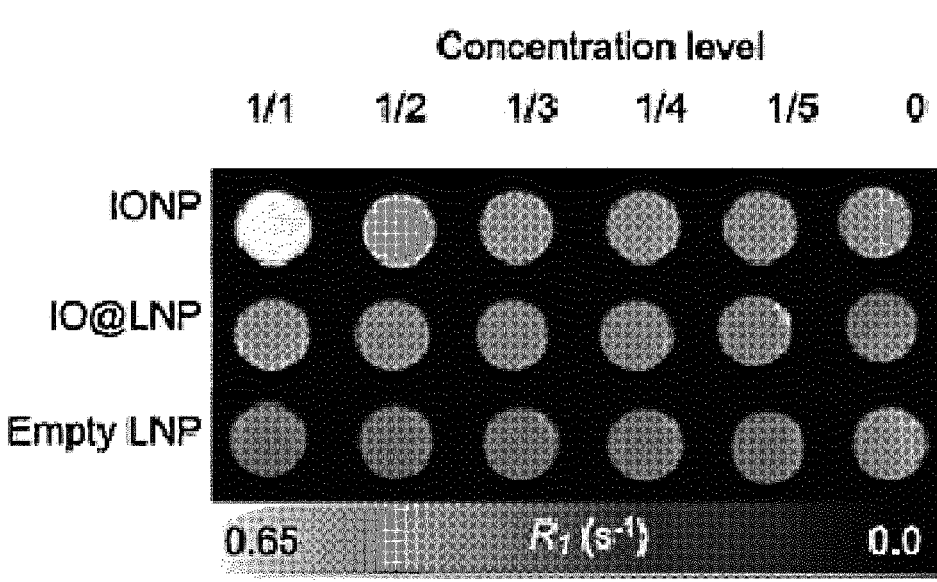
Figure 13B:
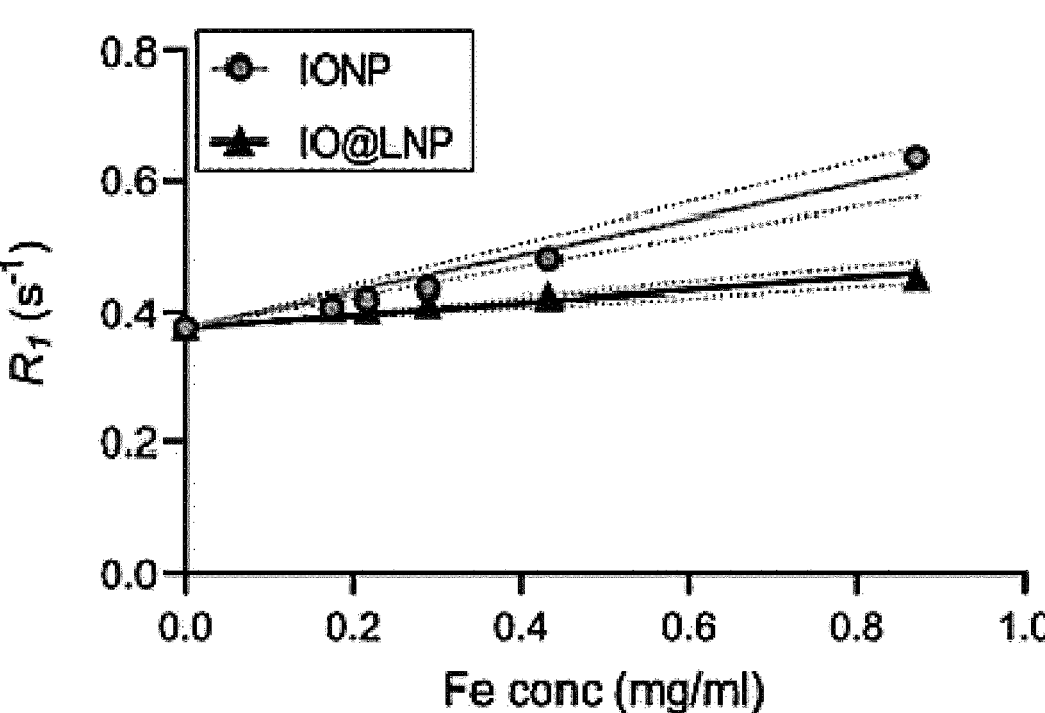
Figure 13C:
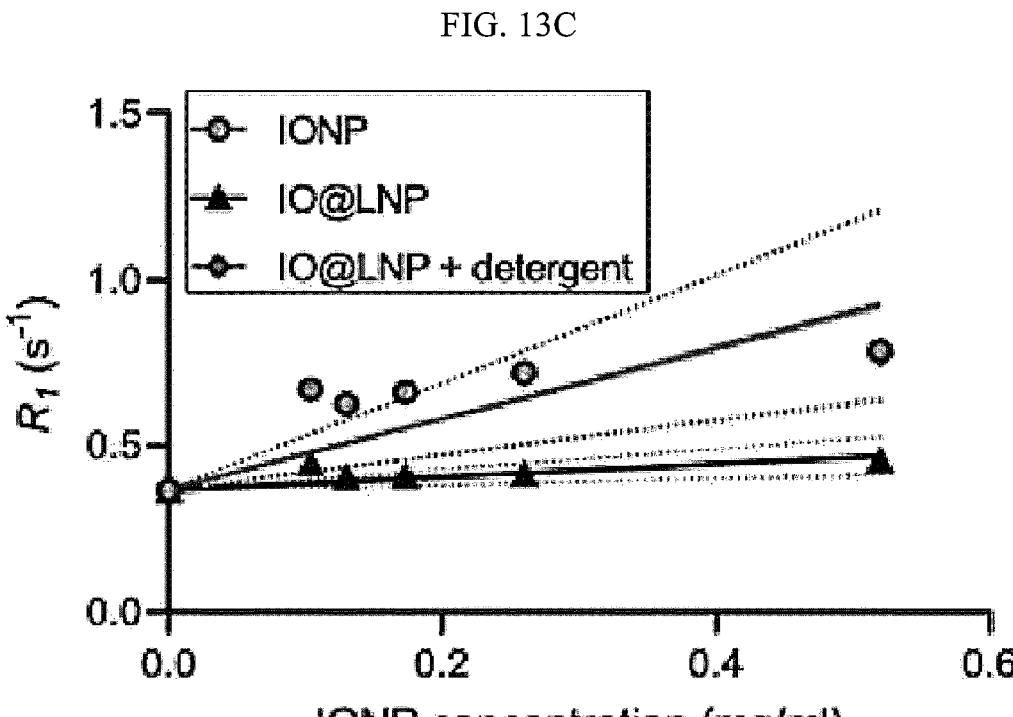
Figure 13D:
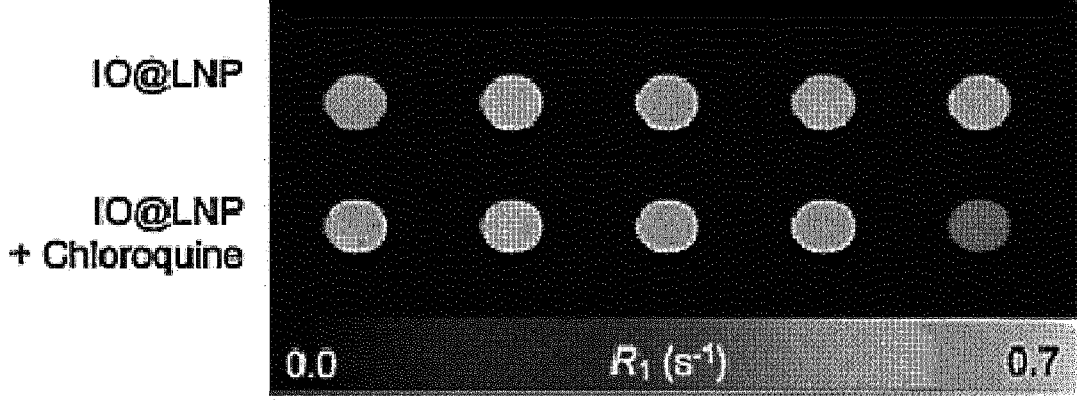
Figure 13E:
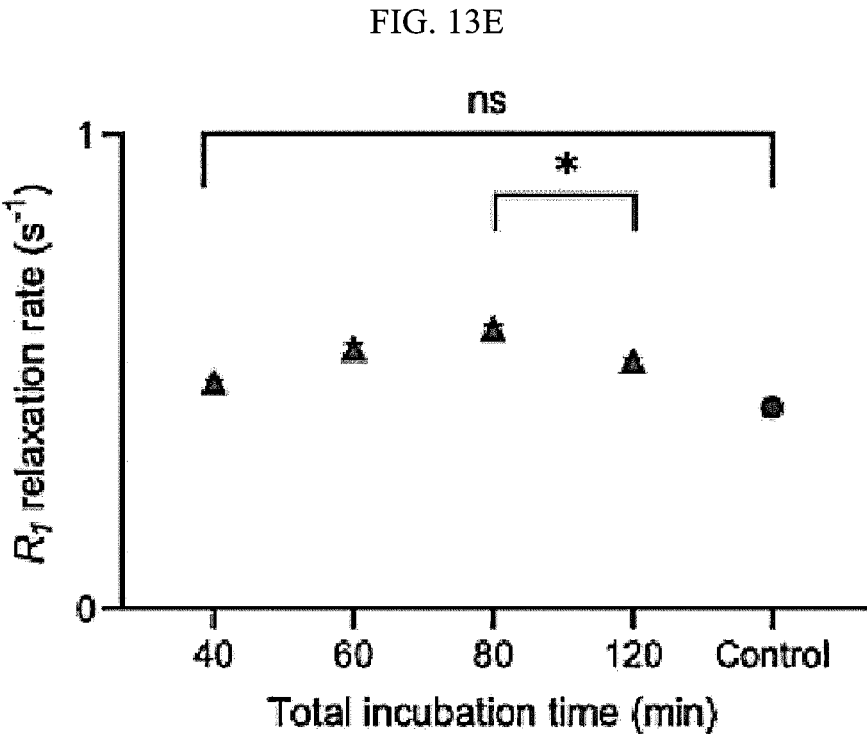
Figure 13F:
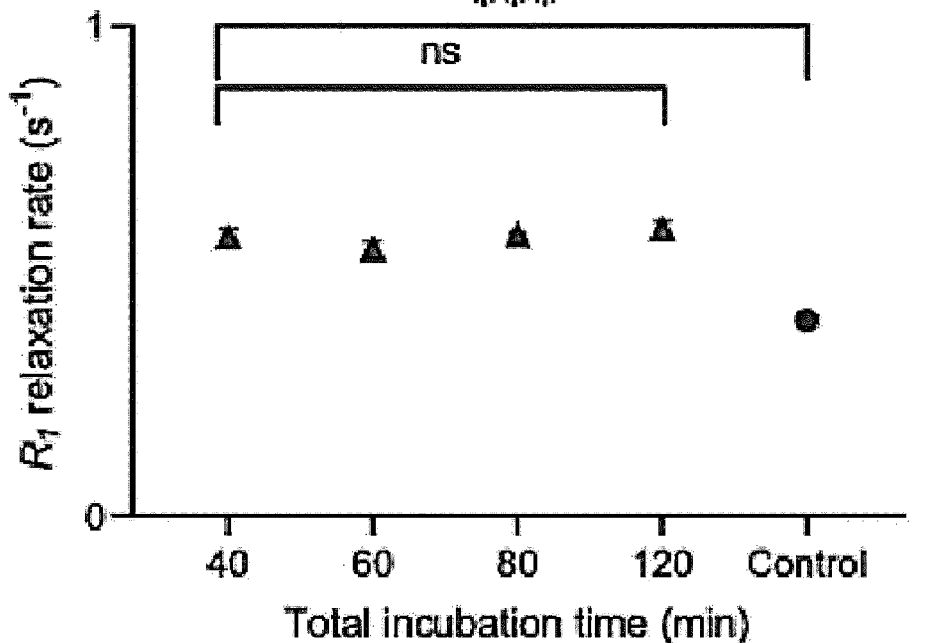

FIGS. 13A to 13F illustrate MR phantom $R_1$ magnetic relaxation rate values and in vitro MRI results. Specifically, FIG. 13A illustrates MR phantom $R_1$ images of IONP, IO@LNP and empty LNP, wherein these images are obtained by performing serial dilutions from 1/1 (0.87 mg IONP and 0 mg total lipid per ml for IONP, 0.87 mg IONP and 4.33 mg total lipid per ml for IO@LNP, and 0 mg IONP and 4.33 mg total lipid per ml for empty LNP) to 1/5 in concentration levels, and a saline sample was represented as 0; FIG. 13B illustrates $R_1$ relaxation rate coefficient value of free IONP (brown, y=0.27532x+0.37587, $R_2$=0.9802) and IONP of IO@LNP (red, y=0.09477x+0.37587, $R_2$=0.9694); FIG. 13C illustrates results of MR phantoms according to whether or not Triton X-100 detergent was treated with IO@LNPs compared to IONPs, and specifically illustrates $R_1$ magnetic relaxation rate values of free IONPs (brown, y=1.0901x+0.36387, $R_2$=0.6371), IONP of IO@LNPs not treated with detergent (red, y=1.0417x+0.37296, $R_2$=0.6297), and IONPs of IO@LNPs treated with detergent (blue, y=0.2012x+0.36387, $R_2$=0.5204), wherein a linear regression curve having a fixed y-intercept is represented in FIG. 13C; FIG. 13D illustrates $R_1$ magnetic relaxation rate values of IO@LNP and IO@LNP+chloroquine in in vitro MRI experiments; FIG. 13E illustrates $R_1$ magnetic relaxation rate of cell pellets (n=3) treated with IO@LNPs according to the total incubation time; and FIG. 13F represents $R_1$ magnetic relaxation rate of cell pellets (n=3) treated with chloroquine and IO@LNPs according to the total incubation time. In FIGS. 13E and 13F, Control is $R_1$ magnetic relaxation rate value of cells without any treatment.

Figure 14A:
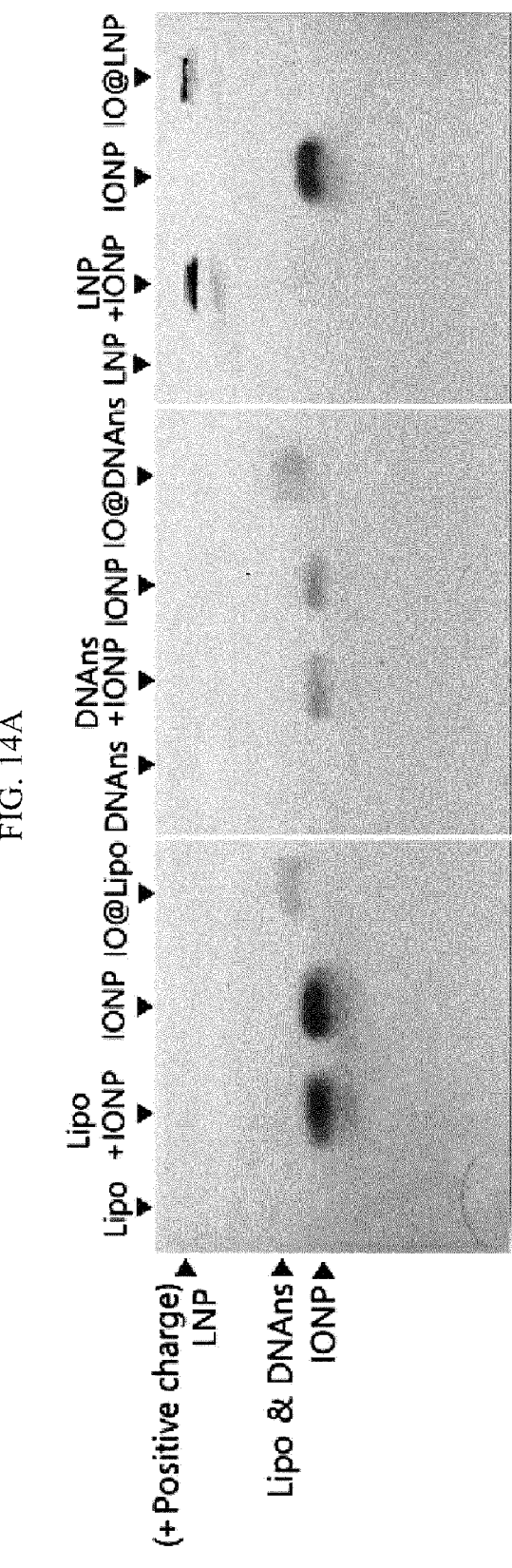
Figures 14B, 14C:
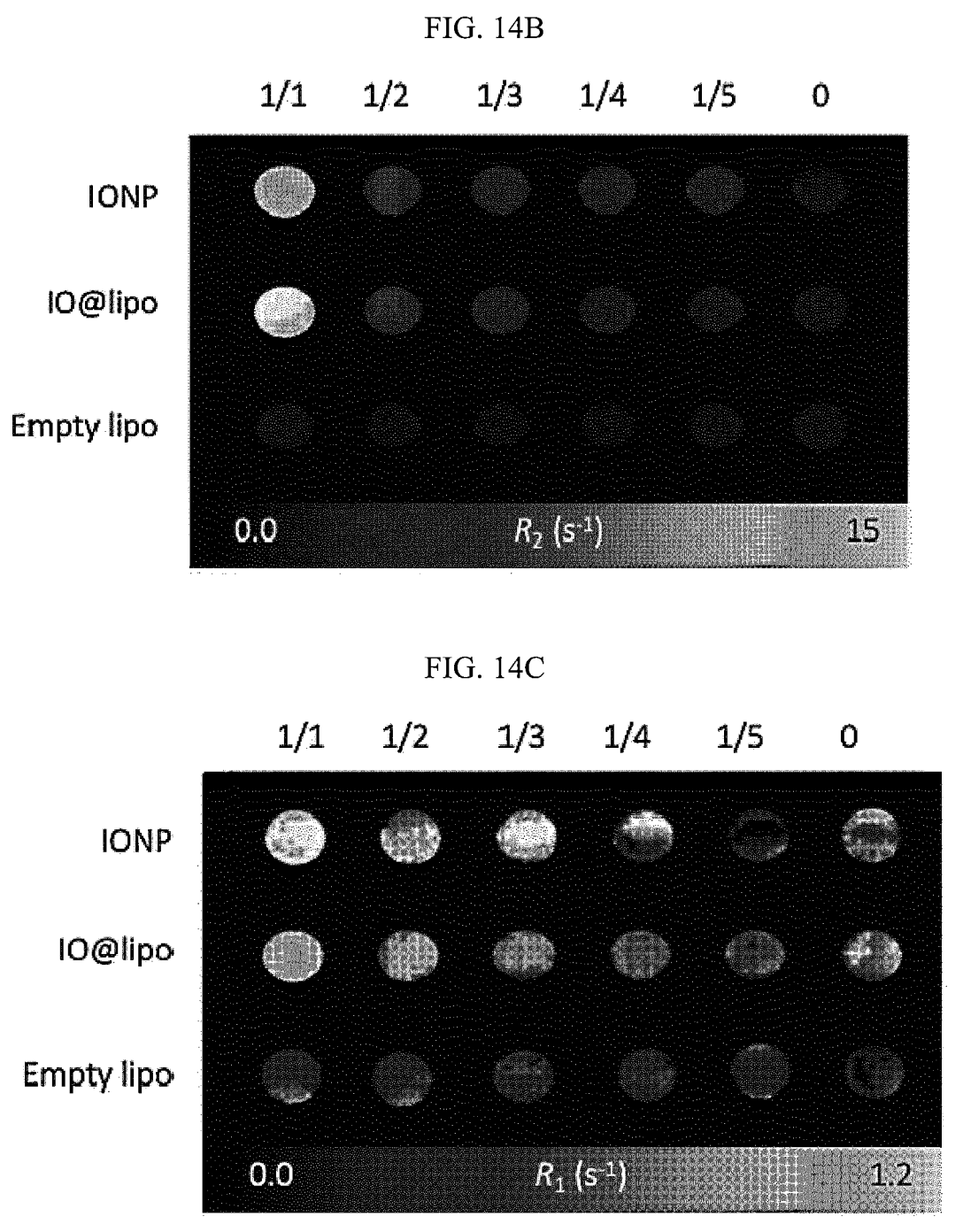

FIGS. 14A to 14C are results of loading IONPs inside various drug delivery particles. Specifically, FIG. 14A illustrates confirmation of carrying by electrophoresis after IONPs were loaded on liposomes, DNA nanostructures and LNPs; FIG. 14B is an MR phantom $R_2$ map image of IONP, IO@lipo (iron oxide-loaded liposomes) and empty liposome (Empty lipo); and FIG. 14C illustrates $R_1$ map image thereof, wherein these images are obtained by performing serial dilutions from 1/1 (0.8 mg IONP and 0 mg total lipid per ml for IONP, 0.8 mg IONP and 4 mg total lipid per ml for IO@lipo, 0 mg IONP and 4 mg total lipid per ml for Empty lipo) to 1/5 in concentration levels, and a saline sample was represented as 0.

DETAILED DESCRIPTION

The present invention relates to a method for quantitatively analyzing endosomal escape efficiency of drug delivery particles, and more specifically, to a method for quantitatively analyzing endosomal escape efficiency of drug delivery particles by measuring magnetic resonance signals (MR signals) reflected by transmitting electromagnetic waves (e.g., radio waves) to cells having iron oxide-loaded particles ingested thereinto using a magnetic resonance imaging device, and obtaining a change rate of magnetic relaxation rate due to a lapse of time from the measurements.

In the present disclosure, the terms "lipid nanoparticle" and "LNP" may be used interchangeably with each other, and refers to a transport vehicle including phospholipid, cholesterol, polyethylene glycol-phospholipid (PEG-phospholipid) and the like. This has applicability as a drug delivery system for delivering drugs into the body.

In the present disclosure, the term "IONP" refers to an iron oxide nanoparticle and may be used interchangeably with "iron oxide."

In the present disclosure, the term "IO (@LNP" refers to an iron oxide-loaded lipid nanoparticle, and "empty LNP" refers to empty lipid nanoparticles without any substance loaded therein.

The present invention provides a method for analyzing endosomal escape efficiency of drug delivery particles, including the steps of: obtaining, in a cell into which particles having iron oxides loaded therein are ingested, a magnetic resonance signal which changes as the iron oxides are released from the particles to the cell: obtaining a graph representing changes in a magnetic relaxation rate due to a lapse of time from the magnetic resonance signal: obtaining a change rate of the magnetic relaxation rate in an arbitrary time interval of the graph; and obtaining an endosomal escape rate of the particles by substituting the change rate of the magnetic relaxation rate into Equation 1 below:

$$\text{[Equation 1]}$$

Endosomal escape rate (%) =

(Change rate of magnetic relaxation rate in cell having particles ingested thereinto ÷ (Magnetic relaxation rate of total iron oxides loaded in particles before endosomal escape − Magnetic relaxation rate of total free iron oxides released from particles due to endosomal escape)) × 100.

The magnetic resonance signal (for example, a longitudinal magnetization signal or a transverse magnetization signal) may be obtained by treating cells with iron oxide-loaded particles, incubating the cells for a predetermined period of time, and then irradiating the cells with radio waves. For example, the cells are treated with iron oxide-loaded lipid nanoparticles, incubated for 10, 20, 30, 40, 60, 80 or 120 minutes, and then the cells are irradiated with radio waves using a magnetic resonance imaging device, thus magnetic resonance signals emitted from the cells may be obtained.

As the iron oxides loaded in the particles are released into the cell through endosomal escape, an intensity of the magnetic resonance signal emitted from the cell (for example, a longitudinal magnetization intensity ($I_z$) or transverse magnetization intensity ($I_{xy}$)) varies.

The magnetic relaxation rate (a longitudinal magnetic relaxation rate ($R_1$) or transverse magnetic relaxation rate ($R_2$)) may be calculated from the measured intensity of the magnetic resonance signal, and pMRI software may be used to calculate the magnetic relaxation rate.

The magnetic relaxation rate may be an $R_2$ magnetic relaxation rate, the change rate of the magnetic relaxation rate may be a decrease rate of the $R_2$ magnetic relaxation rate, and the decrease rate of the $R_2$ magnetic relaxation rate is a decrease amount per unit time of the $R_2$ magnetic relaxation rate in an arbitrary time interval.

The transverse magnetization intensity ($I_{xy}$), which changes as the iron oxides loaded in the drug delivery particles are released into the cell, may be measured, and the changing $R_2$ magnetic relaxation rate value may be calculated from the measurements.

To calculate the $R_2$ magnetic relaxation rate value from the transverse magnetization intensity ($I_{xy}$), the following equation may be used:

$$R_2 = R_{2,0} + r_2 C = \frac{1}{T2}$$

$$I_{xy} = M_{xy}^0 \exp\left\{-\frac{TE}{T2}\right\}$$

(In the equation, $I_{xy}$ is the transverse magnetization intensity, $M_{xy}^0$ is a bulk magnetization vector in a thermal equilibrium state, $R_2$ is a transverse magnetic relaxation rate ($s^{-1}$), $R_{2,0}$ is a basic transverse magnetic relaxation rate ($s^{-1}$) when a contrast agent (iron oxide) is not loaded, $r_2$ is a transverse magnetic relaxation rate per unit concentration of the contrast agent (iron oxide) ($s^{-1}$ [mg/ml]$^{-1}$), C is a concentration of the contrast agent (iron oxide) (mg/ml), and TE is an echo time).

The magnetic relaxation rate may be an $R_1$ magnetic relaxation rate, the change rate of the magnetic relaxation rate may be an increase rate of the $R_1$ magnetic relaxation rate, and an increase rate of the $R_1$ magnetic relaxation rate may be an increase amount per unit time of the $R_1$ magnetic relaxation rate in an arbitrary time interval.

The longitudinal magnetization intensity ($I_z$), which changes as the iron oxides loaded in the drug delivery particles are released into the cell, may be measured, and the changing $R_1$ magnetic relaxation rate value may be calculated from the measurements.

To calculate the $R_1$ magnetic relaxation rate value from the longitudinal axis magnetization intensity ($I_z$), the following equation may be used:

$$R_1 = R_{1,0} + r_1 C = \frac{1}{T1}$$

$$I_z = M_z^0\left[1 - 2\exp\left\{-\frac{TI}{T_1}\right\} + \exp\left\{-\frac{TR}{T_1}\right\}\right]$$

(In the equation, $I_z$ is the longitudinal magnetization intensity, $M_z^0$ a bulk magnetization vector in a thermal equilibrium state, $R_1$ is a longitudinal magnetic relaxation rate ($s^{-1}$), $R_{1,0}$ is a basic longitudinal magnetic relaxation rate ($s^{-1}$) when a contrast agent (iron oxide) is not loaded, $r_1$ is a longitudinal magnetic relaxation rate per unit concentration of the contrast agent (iron oxide) ($s^{-1}$ [mg/ml]$^1$), C is the concentration of the contrast agent (iron oxide) (mg/ml), TI is an inversion time(s), and TR is a repetition time(s).

Using the magnetic relaxation rate values calculated as above, a graph representing changes in a magnetic relaxation rate due to a lapse of time may be obtained. For example, it is possible to obtain an $R_2$ graph representing changes in a magnetic relaxation rate due to a lapse of time, such as the graph shown in FIG. 3C.

As the iron oxides loaded in the particles are released into the cell through endosomal escape, the $R_1$ magnetic relaxation rate of the cell is increased and the $R_2$ magnetic relaxation rate is decreased. The endosomal efficiency of the particles may be analyzed by measuring the increase amount per unit time of the $R_1$ magnetic relaxation rate (the increase rate of the $R_1$ magnetic relaxation rate) or the decrease amount per unit time of the $R_2$ magnetic relaxation rate (the decrease rate of the $R_2$ magnetic relaxation rate) in an arbitrary time interval.

The $R_2$ magnetic relaxation rate value of the drug delivery particles loaded with iron oxide nanoparticles has a linear proportional relationship with an amount of the loaded iron oxide nanoparticles. For example, the $R_2$ magnetic relaxation rate value of lipid nanoparticles loaded with 50 iron oxide nanoparticles is ½ of the $R_2$ magnetic relaxation rate value of lipid nanoparticles loaded with 100 iron oxide nanoparticles.

The method for analyzing endosomal escape efficiency of drug delivery particles of the present invention may further include the steps of: obtaining a total concentration of intracellular ingested iron oxides; and obtaining a difference between a total magnetic relaxation rate of the iron oxides loaded in the particles before the endosomal escape and a total magnetic relaxation rate of the iron oxides released from the particles to the cell due to the endosomal escape, by substituting the total concentration of the intracellular ingested iron oxides into Equation 2 below:

$$[Equation\ 2]$$

$$\{(Total\ magnetic\ relaxation\ rate\ of\ iron\ oxides\ loaded\ in\ particles) -$$

$$(Total\ magnetic\ relaxation\ rate\ of\ free$$

$$iron\ oxides\ released\ form\ particles\ to\ cell)\} =$$

$$Intracellular\ iron\ oxide\ concentration \times (Magnetic\ relaxation$$

$$rate\ per\ unit\ concentration\ of\ iron\ oxides\ loaded\ in\ particles -$$

$$Magnetic\ relaxation\ rate\ per\ unit\ concentration\ of\ free\ iron\ oxides).$$

For example, by substituting the total concentration of the intracellular ingested iron oxides into Equation 2 above, a difference between a total $R_2$ magnetic relaxation rate of iron oxides loaded in the particles before the endosomal escape and a total $R_2$ magnetic relaxation rate of iron oxides released from the particles to the cell due to the endosomal escape may be obtained.

As a method for obtaining the intracellular iron oxide concentration, methods known in the art may be used, for example, IVIS analysis, ICP-MS analysis, isotope quantitative analysis, and the like may be used.

In one embodiment of the present invention, the intracellular iron oxide concentration was obtained by substituting a mass of iron oxides treated during lipid nanoparticle preparation, the iron oxide loading efficiency of lipid nanoparticles, an intake rate of lipid nanoparticles by cell, and a volume of a cell suspension into Equation 3 below:

$$[Equation\ 3]$$

$$Intracellular\ iron\ oxide\ cocentration =$$

$$\{(Mass\ of\ iron\ oxides\ treated\ during\ particle\ preparation) *$$

$$(Iron\ oxide\ loading\ efficiency\ of\ particles) \times$$

$$(Volume\ of\ particles\ treated\ in\ cell \div Volume\ of\ synthesized\ particles) *$$

$$(Intake\ rate\ of\ lipid\ nanoparticles\ by\ cell)\} \div (Volume\ of\ suspension).$$

The method for measuring the intake rate of particles by the cell is not limited, and to determine the intake rate of particles by the cell in one embodiment of the present invention, a ratio of particles that could not be ingested by the cell was calculated by measuring a total fluorescence intensity of particles (IONP@LNP/DiD) labeled with a fluorescent dye (DiD) and a fluorescence intensity of the particles that could not be ingested by the cell (a fluorescence intensity of supernatant), and then the intake rate of the particles by the cell was calculated through the results.

$$Intake\ rate\ of\ lipid\ nanoparticles\ by\ cell\ (\%) =$$

$$100 \times \left(1 - \frac{\sum FLU_{supernatant}}{\sum FLU_{particle}}\right)$$

(In the equation, $FLU_{supernatant}$ is the fluorescence intensity of the supernatant, and $FLU_{particle}$ is the total fluorescence intensity of lipid nanoparticles labeled with a fluorescent dye).

In one embodiment of the present invention, the iron oxide loading efficiency of lipid nanoparticles was measured to about 99.88%, and an intracellular iron oxide mass was calculated as follows: Intracellular iron oxide mass={(Mass of iron oxides added during lipid nanoparticle preparation)× (Volume treated in cell based on volume of synthesized lipid nanoparticles)×(Intake rate of lipid nanoparticles by cell)}.

In one embodiment of the present invention, "$R_2$ magnetic relaxation rate per unit concentration of free iron oxides," that is, $r_2$ of free iron oxides was obtained by measuring a magnetic resonance image signal according to the concentration of free iron oxides and converting it into $R_2$ magnetic relaxation rate per unit concentration.

In one embodiment of the present invention, using a difference between an $R_2$ magnetic relaxation rate of iron oxide-loaded lipid nanoparticles and an $R_2$ magnetic relaxation rate of empty lipid nanoparticles, which are obtained by measuring a magnetic resonance image signal according to the iron oxide concentration of the iron oxide-loaded lipid nanoparticles and a magnetic resonance image signal of the empty lipid nanoparticles, and converting them into the $R_2$ magnetic relaxation rates, an "$R_2$ magnetic relaxation rate per unit concentration of iron oxides loaded in the lipid nanoparticles," that is, $r_2$ of iron oxides loaded in the lipid nanoparticles was obtained.

The method for analyzing endosomal escape efficiency of drug delivery particles of the present invention may further include the step of preparing iron oxide-loaded particles. For preparation of the iron oxide-loaded particles, by allowing a lipid solution and an iron oxide solution to meet at a predetermined speed through a T-junction method, for example, these particles may be prepared.

The method for analyzing endosomal escape efficiency of drug delivery particles of the present invention may further include the step of preparing iron oxides.

The preparation of iron oxides may include the steps of: mixing and heating $FeCl_3$, diethylene glycol and sodium citrate; and additionally mixing acetate to the heated mixture, followed by heating the mixture.

The type of drug delivery particles is not particularly limited as long as they are particles capable of loading iron oxides therein, and may be any one selected from the group consisting of, for example, lipid nanoparticles, liposomes, micelles, polymer nanoparticles, dendrimer nanoparticles, DNA nanostructures, metal nanoparticles, carbon nanotubes, fullerenes and virus-like particles (VLPs).

The drug delivery particles may have a size appropriately selected depending on the type of particles. For example, they may have a size of 30 to 500 nm, 40 to 300 nm, 50 to 250 nm or 50 to 200 nm.

The iron oxides loaded in the drug delivery particles may have a size appropriately selected depending on the size of the drug delivery particles. For example, they may have a size of 1 to 25 nm, 1 to 20 nm or 5 to 20 nm.

Hereinafter, the present invention will be described in more detail through examples.

1. Method

1.1. Material

Fluorescent dyes including anhydrous ethanol (EtOH), sodium acetate (NaAc), acetic acid (AcOH), ferric chloride hexahydrate ($FeCl_3 \cdot 6H_2O$), sodium citrate tribasic dihydrate ($Na_3Cit \cdot 2H_2O$), sodium acetate anhydrous ($CH_3COONa$), diethylene glycol (DEG), 1,2-distearoyl-sn-glycero-3-phosphocholine (18:0 PC (DSPC)), 1,2-di-O-octadecenyl-3-trimethylammonium propane (chloride salt) (DOTMA), cholesterol and 1,1'-dioctadecyl-3,3,3',3'-tetramethylindodecarbocyanine, 4-chlorobenzenesulfonate (DiD) were purchased from Sigma Aldrich, Korea. In addition, (1,2-dis-tearoyl-sn-glycero-3-phosphoethanolamine-N-[methoxy (polyethylene glycol)-5000])(DSPE-mPEG5k) was purchased from Creative PEGWorks. PD-10 column was purchased from Cytiva. Finally, Spectra/Por2™ semipermeable dialysis tube with a molecular weight cutoff (MWCO) of 12-14 kD was purchased.

1.2. Solvothermal Synthesis of Iron Oxide Nanoparticles (IONPs)

Citrate-stabilized ultrasmall iron oxide nanoparticles (IONPs) were synthesized by the following method. First, $FeCl_3 \cdot 6H_2O$ (270.25 mg; 1.00 mmol) and 10 ml of DEG were placed into a three-neck round bottom flask and dissolved while stirring at 1,000 rpm. After $FeCl_3$ was completely dissolved in DEG, $Na_3Cit \cdot 2H_2O$ (117.75 mg: 0.40 mmol) was added to the solution and heated in a heating mantle at 80° C. for 2 hours. Thereafter, sodium acetate anhydrous (328 mg; 4.00 mmol) was added to the solution and heated to 200° C. for 4 hours. Then, the mixture was cooled to 100° C. The mixture was divided equally into 5 tubes and 20 ml of EtOH was added to each tube. After centrifugation at 8,500 rpm for 30 minutes, the supernatant was removed. Thereafter, 15 ml of EtOH was added, and resuspension of the iron oxide precipitate, centrifugation at 7,000 rpm for 30 minutes, and removal of the supernatant were repeated three times in this order. Finally, EtOH was dried and completely evaporated overnight at room temperature.

1.3. Preparation of Iron Oxide Nanoparticle-loaded Lipid Nanoparticles (IO@LNPs)

Lipids (DOTMA, DSPC, DSPE and cholesterol) and PEG were dissolved in 1 ml of EtOH.

Thereafter, 1 ml of NaAc (pH 4.0) was mixed with 1 ml of EtOH at a predetermined flow rate at both ends using a T-junction and a Gemini 88 Plus Dual Rate Syringe Pump (KDS). The pH was determined by mixing NaAc and AcOH in an appropriate ratio in a pH meter. Thereafter, a final solution and a buffer solution of PBS were exchanged by a semipermeable dialysis tube.

IO@LNP/DID labeled with DiD fluorescent dye followed the same lipid composition as IO@LNP except that 4 μl of DiD was added to the lipid solution.

To synthesize liposomes (IO@lipo) loaded with iron oxide nanoparticles (IONPs), DOTMA was excluded while other components were kept the same as IO@LNPs.

Fabrication of DNA nanospheres (IO@DNAns) loaded with IONPs was followed the standardized protocol.

1.4. Characteristics of iron Oxide Nanoparticles (IONPs) and Iron Oxide Nanoparticle-loaded Lipid Nanoparticles (IO@LNPs)

Hydrodynamic sizes of IONPs and IO@LNPs were evaluated with dynamic light scattering (DLS) by a Zetasizer. In addition, the size distribution of the obtained IONPs was confirmed using transmission electron microscopy (TEM) images. Zeta potentials of IONPs, IO@LNPs and empty LNPs were measured by a DTS1070 capillary zeta cell equipped with a Zetasizer. Fourier transform infrared (FT-IR) spectra of IONPs were obtained using a Routine FT-IR spectrometer (Bruker). A vibrating sample magnetometer (VSM) test was performed with VSM-7410 to confirm superparamagnetic properties of IONPs. Cryo-TEM was used to confirm whether IONPs were loaded in the IO@LNPs. Stabilities of IONPs and IO@LNPs were estimated by acquiring hydrodynamic sizes thereof at different time points using various solvents including distilled water, PBS and Roswell Park Memorial Institute 1640 growth medium (RPMI growth medium). To obtain the fluorescence intensity of each particle labeled with DiD dye, a SYN-ERGY H1 microplate reader (BioTek) was used while excitation and emission wavelengths were fixed at 644 and 674 nm.

1.5. MR Phantom

To understand MR properties of IONP, IO@LNP and empty LNP, MR phantom results were obtained by performing serial dilutions from 1/1 (0.87 mg IONP and 0 mg total lipid per ml for IONP: 0.87 mg IONP and 4.33 mg total lipid per ml for IO@LNP, and 0 mg IONP and 4.33 mg total lipid per ml for empty LNP) to 1/5 in concentration levels.

7.0 Tesla Micro MRI was used for MR phantom imaging. $R_1$ relaxation rate was measured using an inversion recovery FLASH (IR FLASH) sequence (FOV: 30 mm*52.5 mm; matrix: 128*128; slice thickness: 2.0 mm; TR: 8 ms; TE: 0 ms; TI: 20 to 4804 ms, average: 1, echo: 300, no fat saturation; scan time: 16 minutes). In addition, the $R_2$ relaxation rate was measured using a multi-echo spin-echo sequence (MEMS) (FOV: 35 mm*52.6 mm; matrix: 128*128; slice thickness: 2.0 mm; TR: 5000 ms; TE: 9 to 9 2700 ms; average: 2, echo: 300, no fat saturation; scan time: 22 minutes).

To confirm whether MR parameters of IO@LNPs became those of IONPs by lipid removal as expected, Triton X-100 was used as a detergent. To this end, Triton X-100 was treated in IO@LNP solution at 37° C. for 10 minutes. Thereafter, the solution was cooled at room temperature for 5 minutes. Finally, MR phantom experiments were performed on the samples.

1.6. Taking Confocal Images

DiD-labeling of LNP surface was first performed. 70,000 4T1 cells were transferred to confocal dishes and incubated overnight. Two materials were treated simultaneously or separately at the appropriate time so that IO@LNP treatment time was 0, 20, 40, 60 or 80 minutes, and Hoechst33342 (0.5 μl per dish) treatment time was 5 minutes. After washing the particles and preparations, the samples were observed under a confocal fluorescence microscope.

1.7. In vitro MRI

4T1 cells were cultured for 40 minutes in a medium supplemented with IO@LNPs. After aspirating the medium, each cell was further cultured for 0, 20, 40 and 80 minutes, respectively, to obtain cells incubated for a total of 40, 60, 80 and 120 minutes. Thereafter, the medium was aspirated, the cells were washed once with DPBS, and treated with trypsin-EDTA, then the cells were incubated for 2 minutes. Cell pellets were obtained by centrifugation and resuspended in 1 ml DPBS. Total cell density and cell survival rate for each sample were calculated with a hemocytometer following the standard trypan-blue staining protocols. The cells were transferred to a 1.5 ml EP tube and the pellets were obtained by centrifugation at 500 rcf for 10 minutes. Then, the pellets were resuspended in 4% paraformaldehyde (PFA) at room temperature for 15 minutes. Thereafter, centrifugation was performed at 500 rcf for 10 minutes and resuspension in DPBS was repeated twice. The pellets were collected, resuspended in 50 µl DPBS and transferred to a PCR tube. After waiting long enough for the cells to be completely precipitated, the supernatant was removed. The obtained samples were stored at 4° C. $R_1$ and $R_2$ magnetic relaxation rates were obtained from IR FLASH and MEMS, respectively, as described in the MR phantom experiment.

In addition, after treating the cell pellets with fluorescence, the intake rate of lipid nanoparticles by cells was analyzed using fluorescence photometry. The total fluorescence intensity of lipid nanoparticles (IONP@LNP/DiD) labeled with a fluorescent dye (DiD) and the fluorescence intensity of lipid nanoparticles that could not be ingested by the cells (fluorescence intensity of the supernatant) were measured, thus to calculate the intake rate of lipid nanoparticles by the cells from the measurements.

Intake rate of lipid nanoparticles by cell (%) =

$$100 \times \left(1 - \frac{\sum FLU_{supernatant}}{\sum FLU_{particle}}\right)$$

(In the equation, $FLU_{supernatant}$ is the fluorescence intensity of the supernatant, and $FLU_{particle}$ is the total fluorescence intensity of lipid nanoparticles labeled with a fluorescent dye).

To obtain the fluorescence intensity of each particle labeled with the DiD dye, a SYNERGY H1 microplate reader (BioTek) was used while excitation and emission wavelengths were fixed at 644 and 674 nm.

1.8. Interpretation of MR results

Determination of $R_1$ magnetic relaxation rate (longitudinal magnetic relaxation rate) and $R_2$ magnetic relaxation rate (transverse magnetic relaxation rate) values and image acquisition of parameters were performed through pMRI software (www.parametricmri.com, Philadelphia, PA, USA).

The longitudinal magnetization intensity ($I_z$) measured through the IR FLASH sequence is calculated as follows:

$$I_z = M_z^0 \left[1 - 2\exp\left\{-\frac{TI}{T_1}\right\} + \exp\left\{-\frac{TR}{T_1}\right\}\right]$$

$$R_1 = R_{1,0} + r_1 C = \frac{1}{T1}$$

(In the equation, $I_z$ is the longitudinal magnetization intensity, $M_z^0$ is a bulk magnetization vector in a thermal equilibrium state, $R_1$ is a longitudinal magnetic relaxation rate (s$^{-1}$), $R_{1,0}$ is a basic longitudinal magnetic relaxation rate (s$^{-1}$) when a contrast agent (iron oxide) is not loaded, $r_1$ is a longitudinal magnetic relaxation rate per unit concentration of the contrast agent (iron oxide) (s$^{-1}$ [mg/ml]$^{-1}$), C is a concentration of the contrast agent (iron oxide)(mg/ml), TI is an inversion time(s), and TR is a repetition time (s).

The transverse magnetization intensity ($I_{xy}$) measured through the MEMS sequence is calculated as follows:

$$I_{xy} = M_{xy}^0 \exp\left\{-\frac{TE}{T2}\right\}$$

$$R_2 = R_{2,0} + r_2 C = \frac{1}{T2}$$

(In the equation, $I_{xy}$ is the transverse magnetization intensity, $M_{xy}^0$ is a bulk magnetization vector in a thermal equilibrium state, $R_2$ is a transverse magnetic relaxation rate (s$^{-1}$), $R_{2,0}$ is a basic transverse magnetic relaxation rate (s$^{-1}$) when a contrast agent (iron oxide) is not loaded, $r_2$ is a transverse magnetic relaxation rate per unit concentration of the contrast agent (iron oxide) (s$^{-1}$ [mg/ml]$^{-1}$), C is the concentration of the contrast agent (iron oxide) (mg/ml), and TE is an echo time).

A ratio a of relaxation rates is calculated as follows:

$$\alpha = \frac{r_2}{r_1}$$

(In the equation, $r_1$ is the longitudinal magnetic relaxation rate per IONP unit concentration (s$^{-1}$ [mg/ml]$^{-1}$), and $r_2$ is the transverse magnetic relaxation rate per IONP unit concentration (s$^{-1}$ [mg/ml]$^{-1}$)).

When the ratio of IONPs loaded in the lipid nanoparticles among total IONPs is θ, a decrease rate (endosomal escape rate) $\partial\theta/\partial t$ of IONPs loaded in lipid nanoparticles due to a lapse of time may be calculated as follows, and through this, it can be seen that the $r_2$ magnetic relaxation rate value does not greatly depend on the ratio of iron oxide nanoparticles to lipids.

$$\frac{dr_2}{dt} = \frac{\partial r_2}{\partial\theta} \times \frac{\partial\theta}{\partial t}$$

$$\frac{\partial^2 r_2}{\partial\theta^2} = 0 \leftrightarrow \frac{\partial r_2}{\partial\theta} = r_{2,loaded} - r_{2,free}$$

Further, degradation or extracellular discharge as well as the endosomal escape rate may be estimated using ultrasmall IONPs that can theoretically be used as T1 and T2 contrast agents using equations below.

$$r_1(t) = \theta r_{1,loaded} + \eta(1-\theta)r_{1,free}$$

$$r_2(t) = \theta r_{2,loaded} + \eta(1-\theta)r_{2,free}$$

$$\therefore \begin{pmatrix} \dfrac{dr_1(t)}{dt} \\ \dfrac{dr_2(t)}{dt} \end{pmatrix} = \begin{pmatrix} r_{1,loaded} & r_{1,free} \\ r_{2,loaded} & r_{2,free} \end{pmatrix} \begin{pmatrix} \dfrac{d\theta}{dt} \\ -\eta\dfrac{d\theta}{dt} \end{pmatrix}$$

1.9. Bio-TEM Image Analysis

4T1 cells were cultured in a T-175 flask for 2 days. Then, the cells were treated with 3 ml of IO@LNPs and further cultured for 40, 60, 80 or 120 minutes. The cells cultured for 40 minutes were washed twice with DPBS. On the other hand, the cells cultured for 60, 80 and 120 minutes were incubated for 40 minutes, washed once with DPBS, and then further incubated in 13 ml RPMI growth medium for the remaining time. Thereafter, the cells were washed once more with DPBS. 4 ml of trypsin-EDTA was added to the cells and incubated for 2 minutes. 11 ml medium was added and the pellets were collected by centrifugation. The supernatant was aspirated and the cells were resuspended in 1 ml DPBS. Then, the pellets were collected by centrifugation at 500 rcf for 10 minutes. To prepare a sample for an excess amount of IONPs, a concentration of IONPs 3.5 times the amount loaded in IO@LNPs was added to the cells and incubated for 40 minutes again. For the control, all procedures were performed in the same manner as the 40-minute sample except that the nanoparticles were not treated.

The pre-treatment process of the sample was divided into 9 steps such as Karnovsky fixation, En Bloc staining, embedding and the like. All methods were performed according to the method recommended by the manufacturer. Thereafter, a thin film step was continued with a microtome and Bio-TEM images were acquired.

To perform semiquantitative analysis with images, three criteria were set to define IO@LNPs in cellular vesicles as follows. First, a signal of interest should be significantly lower than the periplasmic signal. Second, a diameter of the cavity should range from 100 to 200 nm. Lastly, the cavity should include at least 3 black dots. The cavity may be defined as IO@LNPs in the cellular vesicles.

1.10. Tomocube Analysis $1 \times 10^5$ cells were seeded in Tomodish along with 3 ml RPMI growth medium. Then, the cells were cultured for 2 days. Thereafter, the cells was treated with 300 μl IO@LNP/DID for 40 minutes. Then, the cells were observed vertically. All parameters were set to default values.

1.11. In vivo Experiment

Four normal Balb/c mice were injected with 200 μl IO@LNP/DiD through the tail vein. In vivo fluorescence images were obtained through an in vivo imaging system (IVIS) at 0, 0.5, 1, 2, 3, 6, 12 and 24 hours after injection. Finally, the fluorescence intensity of the liver for each mouse was assessed by an appropriate ROI around the liver.

Similarly, one normal Balb/c mouse was injected with 500 μl IO@LNP/DiD through the tail vein. In addition, $R_2$ maps were obtained through 7.0 Tesla Micro MRI at 1, 1.7, 2.4 and 6 hours after IO@LNP/DiD injection along with pre-treatment. $R_2$ relaxation rate was measured using a multi-echo spin-echo sequence (MEMS) (FOV: 35 mm*35 mm; matrix: 128*128; slice thickness: 2 mm; TR: 5000 ms; TE: 12 to 360 ms; average: 4, echo: 30, fat saturation: O, scan time: 43 minutes).

2. Results

2.1. Characteristics of IONPs and IO@LNPs

Ultrasmall IONPs were synthesized without surface coating such as polyethylene glycol (PEG) modification to secure higher $R_2$ relaxation rate and efficient encapsulation of LNPs. The morphology and size distribution of IONPs were observed by TEM and DLS. TEM images using negative staining showed that IONPs had a uniformly dispersed ultrasmall size distribution (FIG. 2A). The hydrodynamic size of IONPs was 2.289±0.641 nm (mean±SD), which is consistent with the reference value of 1.9 nm (FIG. 2C). At the same time, the polydispersity index (PDI) of IONPs was 0.235. The zeta potential (surface charge) of IONPs was −17.7±5.09 mV (mean±SD), which means that there is strong repulsion between the IONPs due to sufficient negative charge (FIG. 2D). The Fourier transform infrared spectra of IONPs exhibited peaks similar to the reference, such as 1,587 and 1,372 cm$^{-1}$, which may be caused by stretching vibrations of the conjugated C=O and C—O bonds (FIG. 7A). In addition, the peaks around 2,900 cm$^{-1}$ and 1,100 cm$^{-1}$ represent stretching vibrations of the —CH2- group and C—O bond from sodium citrate, respectively. The results of vibrating sample magnetometer (VSM) showed the superparamagnetic properties of IONPs (FIG. 7B). The normalized saturation moment of IONPs was about 3 emu/g, as can be seen in the reference. This shows that IONPs may be used as a T2 contrast agent. In addition, IONPs were shown to be stable within 7 hours in various media including distilled water, phosphate-buffered saline (PBS), and RPMI growth medium containing 10% fetal bovine serum (FBS) and 1% antibiotic-antimycotic (FIG. 8A). In the RPMI growth medium, IONPs showed slight instability after one day due to the lack of surface coating. An increase in the hydrodynamic size indicates protein binding from the medium to the particles.

The synthesized IONPs were encapsulated in LNPs. IO@LNPs were prepared from DOTMA, DSPC, DSPE-PEG$_{5k}$ and cholesterol with a uniform size using a fluid-based device. Cryo-TEM showed that IONPs were successfully loaded in LNPs (FIG. 8B). Electrophoresis results for IONPs and IO@LNPs also showed that the added IONPs were loaded in LNPs (FIG. 8C). The size of the LNPs loaded with IONPs (IO@LNP) was 93.13±30.66 nm (mean±SD) with a PDI of 0.166 (FIG. 2C). In addition, the zeta potential of IO (@LNPs was 6.11±7.18 mV (mean±standard deviation) (FIG. 2D). IO@LNPs showed a more negative surface charge than the empty LNPs of 11.9±6.01 mV (FIG. 9C). This showed that negatively charged IONPs and cationic lipids were attracted to each other, thereby reducing the effective number of cationic lipids on the IO@LNP surface. In addition, IO@LNPs were shown to be stable in various media within a week (FIG. 8B). The size and PDI remained relatively constant over time. DiD-labelled IO@LNP (IO@LNP/DiD) and sulfo-cy5.5-loaded IO@LNP (IO@LNP/Sulfo-cy5.5) were prepared for in vitro experiments.

2.2. MR Phantom

To secure better resolution and excellent contrast effect, MR imaging equipment with a high magnetic field of 7.0 Tesla (T) was used.

When exploring the $R_2$ map of IO@LNP according to the ratio of IONPs (mg) to lipids (mg), it was shown that the transverse magnetic relaxation rate ($r_2$) per unit concentration of IONPs ranged from 0.1 mg IO/mg lipid to 0.2 mg IO/mg lipid IO@LNP (p-value=0.51) (FIG. 2E). This indicates that the magnetic moment no longer changes significantly when IONPs are loaded in LNPs, and $r_2$ is constant regardless of the ratio of iron oxide nanoparticles to lipids. Further, this may also be described by the following equation:

$$\frac{\partial^2 r_2}{\partial \theta^2} = 0 \leftrightarrow \frac{\partial r_2}{\partial \theta} = r_{2,loaded} - r_{2,free}$$

(In the equation, $r_2$ is a transverse magnetic relaxation rate ($s^{-1}$) per unit concentration of IONPs, $r_{2,loaded}$ is a transverse magnetic relaxation rate ($s^{-1}$) per unit concentration of iron oxide nanoparticles (IONPs) loaded in LNPs, $r_{2,free}$ is a transverse magnetic relaxation rate ($s^{-1}$) per unit concentration of free iron oxide nanoparticles (IONPs), and $\theta$ is a ratio of IONPs loaded in LNPs among total IONPs.

Table 1 shows the MR sequence characteristics in the MR phantom according to the ratio of IONPs to lipids, and Table 2 shows the MR parameters of IO@LNPs in the $R_2$ map according to the ratio of IONPs to lipids.

TABLE 1

|  | $R_2$ map |
| --- | --- |
| Sequence | MEMS |
| FOV (mm) | 65 |
| Matrix | 128 × 128 |
| Slice Thickness (mm) | 2 |
| TR (ms) | 5000 |
| TE (ms) | 9-2700 |
| TI (ms) | — |
| Average | 2 |
| Echo | 300 |
| Fat Saturation | No |
| Scan Time (min) | 22 |

TABLE 2

|  | 0.1 mg IO/mg lipid IO@LNP | 0.2 mg IO/mg lipid IO@LNP | Saline |
| --- | --- | --- | --- |
| $R_2(s^{-1})$ in 1/1 | 2.22476 | 2.74949 | 0.73221 |
| $R_2(s^{-1})$ in 1/2 | 1.43608 | 1.76211 | — |
| $R_2(s^{-1})$ in 1/3 | 1.12056 | 1.34028 | — |

TABLE 2-continued

|  | 0.1 mg IO/mg lipid IO@LNP | 0.2 mg IO/mg lipid IO@LNP | Saline |
| --- | --- | --- | --- |
| $R_2(s^{-1})$ in 1/4 | 0.96463 | 1.12349 | — |
| $R_2(s^{-1})$ in 1/5 | 0.89962 | 1.01840 | — |
| IONP conc (mg/ml) 1/1 | 0.18735 | 0.25833 | — |
| $r_2(s^{-1}[mg/ml]^{-1})$ | 6.97390 ± 0.30830 | 7.23820 ± 0.25260 | — |

All samples were dissolved in saline.
The $r_2$ values of IO@LNP are $r_2$ values of IO.

In the $R_2$ map results, the transverse magnetic relaxation rate ($r_2$) per unit concentration of IONPs was greater for IO@LNP than for IONP (FIGS. 2F-2G, and FIG. 11A). This is expected to be due to a synergistic effect on the magnetic moment between adjacent IONPs in IO@LNPs. The increase in $r_2$ according to the size of IONPs was reported in a previous paper. Meanwhile, it was shown that the longitudinal magnetic relaxation rate ($r_1$) per unit concentration of IONPs was smaller for IO@LNP than for IONP (FIG. 11B, and FIGS. 13A and 13B). This may be due to a low radio frequency (RF) energy transfer efficiency caused by the limited operation of IONPs loaded in IO@LNPs.

The MR parameters of R1 map and R2 map for IONPs, empty LNPs and IO@LNPs are shown in Tables 3 and 4. Table 3 shows the MR sequence characteristics, and Table 4 shows the MR parameters of IONPs, empty LNPs and IO@LNPs.

TABLE 3

|  | $R_1$ map | $R_2$ map |
| --- | --- | --- |
| Sequence | FLASH | MEMS |
| FOV (mm) | 30 × 52.5 | 35 × 52.5 |
| Matrix | 128 × 128 | 128 × 128 |
| Slice Thickness (mm) | 2 | 2 |
| TR (ms) | 8 | 5000 |
| TE (ms) | 0 | 9-2700 |
| TI (ms) | 20-4804 | — |
| Average | 1 | 2 |
| Echo | 300 | 300 |
| Fat Saturation | X | X |
| Scan Time (min) | 16 | 22 |

TABLE 4

|  | IONP | Empty LNP | IO@LNP | Saline |
| --- | --- | --- | --- | --- |
| $R_1(s^{-1})$ in 1/1 | 0.63696 | 0.35635 | 0.44988 | 0.37587 ± 0.02180 |
| $R_1(s^{-1})$ in 1/2 | 0.48092 | 0.35065 | 0.42152 | — |
| $R_1(s^{-1})$ in 1/3 | 0.43543 | 0.35624 | 0.40992 | — |
| $R_1(s^{-1})$ in 1/4 | 0.41732 | 0.35558 | 0.40299 | — |
| $R_1(s^{-1})$ in 1/5 | 0.40670 | 0.35140 | 0.40382 | — |
| $r_1(s^{-1}[mg/ml]^{-1})$ | 0.27486 ± 0.01764 | — | 0.13288 ± 0.01412 | — |
| $R_2(s^{-1})$ in 1/1 | 3.02159 | 1.20190 | 6.26705 | 1.05491 ± 0.09108 |
| $R_2(s^{-1})$ in 1/2 | 1.93890 | 1.02397 | 3/30333 | — |
| $R_2(s^{-1})$ in 1/3 | 1.62390 | 0.98006 | 2.53705 | — |
| $R_2(s^{-1})$ in 1/4 | 1.47685 | 0.99272 | 2.22423 | — |
| $R_2(s^{-1})$ in 1/5 | 1.41793 | 1.03431 | 2.08270 | — |
| $r_2(s^{-1}[mg/ml]^{-1})$ | 2.18343 ± 0.05207 | — | 5.69480 ± 0.16000 | — |
| IONP conc (mg/ml) 1/1 | 0.87000 | — | 0.87000 | — |
| α | 7.94379 | — | 41.9051 | — |

All samples were dissolved in saline. Both $r_1$ and $r_2$ values of IO@LNP are based on the IO loaded in IO@LNP.
The $r_1$ and $r_2$ values of IO@LNP are $r_1$ and $r_2$ values of IO loaded in IO@LNP.

In addition, MR phantom experiments were performed with and without Triton X-100 detergent treatment to demonstrate that, after lipid removal from IO@LNPs, the MR parameters became those of free IONPs (FIG. 2H and FIG. 13C).

The MR parameters after Triton X-100 treatment for IONPs, empty LNPs and IO@LNPs are shown in Tables 5 and 6. Table 5 shows the MR sequence characteristics, and Table 6 shows the MR parameters of IONPs, IO@LNPs without Triton X-100 treatment, and IO@LNPs with Triton X-100 treatment.

TABLE 5

|  | $R_1$ map | $R_2$ map |
|---|---|---|
| Sequence | FLASH | MEMS |
| FOV (mm) | 30 × 52.5 | 35 × 52.5 |
| Matrix | 128 × 128 | 128 × 128 |
| Slice Thickness (mm) | 0.8 | 0.8 |
| TR (ms) | 8 | 5000 |
| TE (ms) | 0 | 9-2700 |
| TI (ms) | 28-4812 | — |
| Average | 1 | 2 |
| Echo | 300 | 300 |
| Fat Saturation | X | X |
| Scan Time (min) | 16 | 22 |

TABLE 6

|  | IONP | IO@LNP w/o Triton X | IO@LNP w/ Triton X | Saline | Trixon X |
|---|---|---|---|---|---|
| $R_1(s^{-1})$ in 1/1 | 0.78708 | 0.45246 | 0.77608 | 0.36387 | 0.37296 |
| $R_1(s^{-1})$ in 1/2 | 0.72194 | 0.41376 | 0.71644 | — | — |
| $R_1(s^{-1})$ in 1/3 | 0.66418 | 0.40526 | 0.66051 | — | — |
| $R_1(s^{-1})$ in 1/4 | 0.62639 | 0.40366 | 0.62364 | — | — |
| $R_1(s^{-1})$ in 1/5 | 0.67231 | 0.44300 | 0.67011 | — | — |
| $r_1(s^{-1}[mg/ml]^{-1})$ | 1.09010 ± 0.21470 | 0.20117 ± 0.04428 | 1.04170 ± 0.20710 | — | — |
| $R_2(s^{-1})$ in 1/1 | 2.78748 | 4.42259 | 2.66428 | 1.19619 | 1.45403 |
| $R_2(s^{-1})$ in 1/2 | 1.93937 | 2.81245 | 2.05870 | — | — |
| $R_2(s^{-1})$ in 1/3 | 1.67159 | 2.29855 | 1.93423 | — | — |
| $R_2(s^{-1})$ in 1/4 | 1.57104 | 2.08791 | 1.92206 | — | — |
| $R_2(s^{-1})$ in 1/5 | 1.56901 | 2.01590 | 2.08751 | — | — |
| $r_2(s^{-1}[mg/ml]^{-1})$ | 3.00840 ± 0.06447 | 6.29220 ± 0.13370 | 2.51790 ± 0.29490 | — | — |
| IONP conc (mg/ml) 1/1 | 0.52 | 0.52 | 0.52 | — | — |

IONP and IO@LNP w/o Triton X were dissolved in saline. IO@LNP w/Triton was dissolved in TritonX.

2.3. In vitro MRI Results

To determine the endosomal escape start point of IO@LNPs, the uptake pattern due to a lapse of time in 4T1 cells was evaluated through confocal imaging using IO@LNP/DiD. The cells were treated with the same amount of IO@LNP/DiD, cultured for different times, and then washed. The following observation results were confirmed through imaging (FIGS. 13A and 13B). As expected, it was shown that intracellular uptake of lipid nanoparticles was rare at 0 minutes, and the lipid nanoparticles appeared to be located mainly on the cell surface at 20 minutes, and were located more in the cytoplasmic region at 40 minutes. Through this, it could be seen that endosomal escape begins to occur between 20 and 40 minutes, and the continued efficiency of endosomal escape was able to be tracked from 40 minutes. Based on this finding, in the in vitro MRI experiment below, the IO@LNP intake time of cells was set to 40 minutes, and the cells were further incubated (0, 20, 40 and 80 minutes) for endosomal escape after the fixed intake time (total incubation time: 40, 60, 80 and 120 minutes) (FIG. 3A).

In the $R_2$ map, a clear decrease in the $R_2$ value was observed with increasing the incubation time, and a group with only the cells exhibited lower $R_2$ than cells treated with IO@LNPs. The endosomal escape efficiency $\partial\theta/\partial t$ was calculated using the following equation (FIGS. 3A-3C, and FIGS. 13D-13F):

$$\frac{\partial\theta}{\partial t} = \frac{1}{C(r_{2,\,loaded} - r_{2,\,free})} \frac{dR_2}{dt} \times 100 = 0.99\% \text{ Escape/min}$$

(In the equation, $\theta$ is a ratio of IONPs loaded in lipid nanoparticles among total IONPs, $dR_2/dt$ is a decrease rate of $R_2$ magnetic relaxation rate of cell ingested with lipid nanoparticles, which is 0.2189 $s^{-1}$/min, $r_{2,loaded}$ is a transverse magnetic relaxation rate per unit concentration of IONPs loaded in LNPs, which is 5.69480 $s^{-1}$ $[mg/ml]^{-1}$, $r_{2,free}$ is a transverse magnetic relaxation rate per unit concentration of free IONPs, which is 2.18343 $s^{-1}$ $[mg/ml]^{-1}$, and C is an average IONP concentration of the cell, which is 6.26847 mg/ml).

To verify that a decrease in the $R_2$ value is caused by the endosomal escape, changes in the $R_1$ value of cells incubated for 40, 60 and 80 minutes were observed. In the above time interval, since the $R_1$ value showed an opposite trend to the $R_2$ value, it was confirmed that the decrease in the $R_2$ value in this time interval was caused by the endosomal escape (FIGS. 3B and 3C, and FIGS. 13D-13F). However, in the cells incubated for 120 minutes, both $R_1$ and $R_2$ values were decreased, thus it could be seen that decomposition of IONPs or extracellular release occurred. Meanwhile, the cell pre-treated with chloroquine showed a constant $R_1$ value from 40 to 120 minutes. Chloroquine promotes endosomal escape, thus it could be seen that the endosomal escape was completed before 40 minutes.

MR parameters are shown in Tables 7 to 9. Table 7 shows the MR sequence characteristics, and Tables 8 and 9 illustrate the MR parameters of cells incubated for a total of 40, 60, 80 and 120 minutes, including the same intake time of 40 minutes after IO@LNP treatment. As a control, the MR parameters of cells alone without IO@LNP treatment were also shown. In Table 9, cells pre-treated with chloroquine were used.

TABLE 7

|  | R$_1$ map | R$_2$ map |
|---|---|---|
| Sequence | FLASH | MEMS |
| FOV (mm) | 40 × 65 | 40 × 65 |
| Matrix | 128 × 128 | 128 × 128 |
| Slice Thickness (mm) | 0.5 | 0.5 |
| TR (ms) | 8 | 5000 |
| TE (ms) | 0 | 9-2700 |
| TI (ms) | 28-4804 | — |
| Average | 1 | 2 |
| Echo | 300 | 300 |
| Fat Saturation | X | X |
| Scan Time (min) | 16 | 22 |

TABLE 8

|  | Incubation for 40 minutes | Incubation for 60 minutes | Incubation for 80 minutes | Incubation for 120 minutes | Cell alone |
|---|---|---|---|---|---|
| Intake rate (%) |  |  | 6.07410 |  |  |
| R$_1$(s$^{-1}$) | 0.47832 ± 0.00694 | 0.54833 ± 0.01263 | 0.58974 ± 0.00929 | 0.52174 ± 0.00859 | 0.42435 ± 0.01711 |
| R$_2$(s$^{-1}$) | 32.0836 ± 5.57606 | 24.0780 ± 3.00415 | 17.2224 ± 1.64582 | 14.0396 ± 0.93145 | 5.52222 ± 0.01786 |
| Intracellular iron oxide concentration (mg/ml) | 2.58 mg (Intracellular iron oxide mass) ÷ 25 μl (Final volume) × 0.067410 (Intake rate of lipid nanoparticles by cell) = 6.26847 (mg/ml) | | | | |

All samples were fixed to agarose gel and then dissolved in DPBS.

30

TABLE 9

|  | Incubation for 40 minutes | Incubation for 60 minutes | Incubation for 80 minutes | Incubation for 120 minutes | Cell alone |
|---|---|---|---|---|---|
| R$_1$(s$^{-1}$) | 0.56891 ± 0.06197 | 0.54358 ± 0.01652 | 0.57253 ± 0.00542 | 0.58498 ± 0.01712 | 0.39925 ± 0.00595 |
| R$_2$(s$^{-1}$) | 20.52434 ± 0.39818 | 14.65528 ± 0.42163 | 16.84697 ± 0.42732 | 16.32473 ± 0.59480 | 16.7101 ± 0.50763 |

All samples were fixed to agarose gel and then dissolved in DPBS.
Chloroquine was treated to promote endosomal escape of LNPs.

2.4. Verification of In Vitro MRI Results Using Bio-TEM Imaging

To confirm in vitro MR performance results, endosomes including black dots were counted by Bio-TEM imaging (FIGS. 4A-4D). No visible endosomes including black dots were observed in 4T1 cells treated with an excess amount of IONPs or not (Control). In addition, cytotoxic pattern due to IONPs did not appear. However, it was confirmed that more endosomes including IO@LNPs were detected at 40 minutes than at later time points (FIG. 4B). In FIG. 4C, a sum of the number of endosomes in an area of 8 μm×8 μm per Bio-TEM image (n=20 images per group) was calculated and proposed. As the total incubation time was increased, the frequency of endosomes was decreased, which corresponded to the decrease in the R2 value (FIG. 4D). In other words, it was confirmed that as endosomal escape occurs over time, the number of endosomes was decreased and the R2 relaxation rate changed. In addition, the cell of 120 minutes released many vesicles in Bio-TEM images, thereby suggesting that R$_2$ decrease at later time points (e.g., after 120 minutes) may be influenced by active exocytosis.

In fluorescence (FL) imaging using Tomocube, IO@LNP/Sulfo-cy5.5 with Sulfo-cy5.5 dye in hydrophilic spaces of the LNPs was observed. IO@LNP/Sulfo-cy5.5 clearly showed that punctuated patterns appear early and more dispersed patterns dominate at later time points (FIG. 5A). In addition, there was no significant cell death form. Further, active movement of fluorescent intracellular endosomes was observed. It is well known that only early endosomal escape results in high motility, such that the active movement of endosomes suggests the presence of early endosomes in which endosomal escape occurs. To further analyze the degree of endosomal escape, the nominal number of endosomes including LNPs was defined as a value obtained by dividing the number of pixels brighter than the 95th percentile (yellow) by the number of pixels brighter than the 60th percentile (green and yellow) (FIG. 5B). Then, a linear relationship between the number of endosomes and the corresponding R$_2$ value appeared (FIG. 5C). In addition, as a result of observing an elbow point after 80 minutes in background fluorescence quantification, it was confirmed that exocytosis occurred only after 80 minutes (FIG. 5D).

2.5. In Vivo Experiment

The validity of the method for analyzing endosomal escape efficiency of the present invention was verified using in vivo imaging. To investigate the biodistribution of IO@LNPs, female mice were intravenously injected with IO@LNP/DIR (200 μl, 0.8 mg IONP/4 mg total lipid/ml PBS) per mouse. IO@LNP-treated mice showed significantly increased fluorescence signals in the liver (n=4, Balb/c mice) (FIGS. 6A and 6B). A region of interest (ROI) was allocated to the IVIS software to measure the fluorescence signals in the liver (FIG. 6C). The LNP signal in the liver 2 hours after injection was 6.3 times higher than that of 1 hour after injection. It was confirmed that the signal reached the peak in the liver 2 hours after injection with IO@LNPs, which means that the injected nanoparticles were greatly accumulated in the liver. It was considered that Kupffer cells in the liver are the main cell type which absorbs nanoparticles, and for an in vivo MR experiment, 2 hours after ingestion of lipid nanoparticles were determined as a reference time point for endosomal escape.

IONPs and IO@LNPs were injected intravenously into mice, respectively, and it was confirmed whether or not endosomal escape from the liver occurs (FIGS. 6D-6E). Consequently, $R_2$ magnetic relaxation rate value was decreased linearly in IO@LNPs-treated mice. Although most IO@LNPs were found in the liver even 24 hours after injection through IVIS, the $R_2$ value was decreased linearly over time, and through this, it could be seen that the $R_2$ value was decreased due to the endosomal escape. Therefore, an endosomal escape rate was calculated by applying the following equation.

$$\frac{dR_2}{dt} \approx C(r_{2,\,loaded} - r_{2,\,free})\frac{\partial \theta}{\partial t}$$

$$\frac{\partial \theta}{\partial t} = \frac{1}{C(r_{2,\,loaded} - r_{2,\,free})}\frac{dR_2}{dt} = 31.9\% \text{ Escape/hr}$$

(In the equation, $dR_2/dt$ is a decrease rate of $R_2$ magnetic relaxation rate of cell ingested with lipid nanoparticles, which is 2.754717 s$^{-1}$/h, $r_{2,loaded}$ is a transverse magnetic relaxation rate per unit concentration of IONPs loaded in LNPs, which is 5.69480 s$^{-1}$ [mg/ml]$^{-1}$, $r_{2,free}$ is a transverse magnetic relaxation rate per unit concentration of free IONPs, which is 2.18343 s$^{-1}$ [mg/ml]$^{-1}$, and C is an average IONP concentration of the tissue, which is measured as 2.4 mg/ml, and the endosomal escape rate calculated through this was 31.9%/hr (=0.53%/min). It was determined that the endosomal escape efficiency, which was about 2 times slower than in the cell unit experiment, was caused by the involvement of in vivo barrier.

2.6. Applicability to Various Drug Delivery Systems

In the method for analyzing endosomal escape efficiency of the present invention, various materials such as liposomes and DNA nanospheres in addition to LNPs may be used as drug delivery systems. It was confirmed that IONPs were loaded in liposomes and DNA nanospheres (FIG. 14A), and MR signal changes similar to IO@LNP were observed in IO@lipo (liposome loaded with IONPs) (FIGS. 14B and 14C). In other words, it was confirmed that not only LNPs but also other drug delivery systems such as liposomes and DNA nanospheres can be used to analyze endosomal escape efficiency.

24

What is claimed is:

1. A method for analyzing endosomal escape efficiency of drug delivery particles, the method comprising:
measuring, in a cell into which particles having iron oxides loaded therein are ingested, a magnetic resonance signal which changes as the iron oxides are released from the particles to the cell;
obtaining a graph representing changes in a magnetic relaxation rate due to a lapse of time from the magnetic resonance signal;
obtaining a change rate of the magnetic relaxation rate in an arbitrary time interval of the graph; and
obtaining an endosomal escape rate of the particles by substituting the change rate of the magnetic relaxation rate into Equation 1 below:

Endosomal escape rate (%)=(Change rate of magnetic relaxation rate in cell having particles ingested thereinto÷(Magnetic relaxation rate of total iron oxides loaded in particles before endosomal escape−Magnetic relaxation rate of total free iron oxides released from particles due to the endosomal escape))×100 [Equation 1].

2. The method according to claim 1, wherein the magnetic relaxation rate is transverse magnetic relaxation rate which is an $R_2$ magnetic relation rate.

3. The method according to claim 1, further comprising:
obtaining a total concentration of intracellular ingested iron oxides; and
obtaining a difference between a total transverse ($R_2$) magnetic relaxation rate of the iron oxides loaded in the particles before the endosomal escape and a total $R_2$ magnetic relaxation rate of the iron oxides released from the particles to the cell due to the endosomal escape, by substituting the total concentration of the intracellular ingested iron oxides into Equation 2 below:

{(Total magnetic relaxation rate of iron oxides loaded in particles)−(Total magnetic relaxation rate of free iron oxides released from particles to cell)}=Intracellular iron oxide concentration× (Magnetic relaxation rate per unit concentration of iron oxides loaded in particles−Magnetic relaxation rate per unit concentration of free iron oxides) [Equation 2].

4. The method according to claim 1, wherein the particles are any one selected from the group consisting of lipid nanoparticles, liposomes, micelles, polymer nanoparticles, dendrimer nanoparticles, DNA nanostructures, metal nanoparticles, carbon nanotubes, fullerenes and virus-like particles.

5. The method according to claim 1, wherein the particles have a size of 50 to 250 nm.

6. The method according to claim 1, wherein the iron oxides have a size of 1 to 20 nm.

* * * * *